(12) United States Patent
McConaughy et al.

(10) Patent No.: US 11,090,244 B2
(45) Date of Patent: *Aug. 17, 2021

(54) PERSONAL CARE COMPOSITIONS AND ARTICLES

(71) Applicant: The Procter & Gamble Company, Cincinnati, OH (US)

(72) Inventors: Shawn David McConaughy, Cincinnati, OH (US); Edward Dewey Smith, III, Mason, OH (US); Dale Gary Kavalew, Evendale, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 342 days.

This patent is subject to a terminal disclaimer.

(21) Appl. No.: 14/315,483

(22) Filed: Jun. 26, 2014

(65) Prior Publication Data

US 2015/0000058 A1 Jan. 1, 2015

Related U.S. Application Data

(60) Provisional application No. 61/840,120, filed on Jun. 27, 2013, provisional application No. 61/840,084, (Continued)

(51) Int. Cl.
*A61K 8/00* (2006.01)
*A61K 8/46* (2006.01)
(Continued)

(52) U.S. Cl.
CPC ............... *A61K 8/466* (2013.01); *A47K 7/03* (2013.01); *A61K 8/02* (2013.01); *A61K 8/42* (2013.01);
(Continued)

(58) Field of Classification Search
CPC .... A61K 8/466; A61K 8/731; A61K 2800/28; A61K 2800/524; A47K 7/03
See application file for complete search history.

(56) References Cited

U.S. PATENT DOCUMENTS 3,689,437 A 9/1972 McLaughlin
4,515,703 A 5/1985 Haq
(Continued)

FOREIGN PATENT DOCUMENTS

CN 1046273 10/1990
CN 1117835 3/1996
(Continued)

OTHER PUBLICATIONS

International Search Report and Written Opinion of the International Searching Authority, PCT/US2014/044206, dated Dec. 31, 2014, 9 pages.

*Primary Examiner* — Necholus Ogden, Jr.
(74) *Attorney, Agent, or Firm* — Kathleen Y. Carter

(57) ABSTRACT

A compliant personal care composition can include i) from about 20% to about 80%, by weight of the composition, of a surfactant; and ii) from about 3% to about 40%, by weight of the composition, of a water insoluble hygroscopic fiber, fine, or filament; wherein the composition has a compliance value of about 0.01 kg/mm to about 1.5 kg/mm or before a simulated use. The composition may also be at least partially surrounded by a substrate and in the form of an article.

14 Claims, 10 Drawing Sheets

Related U.S. Application Data filed on Jun. 27, 2013, provisional application No. 61/840,157, filed on Jun. 27, 2013, provisional application No. 61/918,739, filed on Dec. 20, 2012, provisional application No. 61/886,502, filed on Oct. 3, 2013, provisional application No. 61/886,508, filed on Oct. 3, 2013.

(51) Int. Cl.
| | |
|---|---|
| *A47K 7/03* | (2006.01) |
| *A61Q 19/10* | (2006.01) |
| *A61K 8/60* | (2006.01) |
| *A61K 8/73* | (2006.01) |
| *A61K 8/02* | (2006.01) |
| *C11D 17/00* | (2006.01) |
| *A61K 8/42* | (2006.01) |
| *C11D 3/48* | (2006.01) |
| *A61Q 5/02* | (2006.01) |

(52) U.S. Cl.
CPC ............ *A61K 8/463* (2013.01); *A61K 8/602* (2013.01); *A61K 8/731* (2013.01); *A61Q 19/10* (2013.01); *C11D 3/48* (2013.01); *C11D 17/006* (2013.01); *A61K 2800/28* (2013.01); *A61K 2800/524* (2013.01); *A61K 2800/87* (2013.01); *A61Q 5/02* (2013.01)

(56) References Cited

U.S. PATENT DOCUMENTS

| | | | | |
|---|---|---|---|---|
| 4,603,069 | A | 7/1986 | Haq et al. | |
| 4,953,250 | A | 9/1990 | Brown | |
| 5,066,494 | A | 11/1991 | Becher | |
| 5,132,115 | A | 7/1992 | Wolter et al. | |
| 5,308,180 | A | 5/1994 | Pournoor et al. | |
| RE34,692 | E | 8/1994 | Becher | |
| 5,486,064 | A | 1/1996 | Schulte | |
| 5,537,709 | A | 7/1996 | Taragos | |
| 5,683,971 | A | 11/1997 | Rose et al. | |
| 5,698,475 | A | 12/1997 | Vlasblom | |
| 5,702,992 | A | 12/1997 | Martin et al. | |
| 5,756,081 | A | 5/1998 | Wdowik | |
| 5,839,842 | A | 11/1998 | Wanat et al. | |
| 5,968,852 | A | 10/1999 | Vlasblom | |
| 6,063,390 | A | 5/2000 | Farrell et al. | |
| 6,153,208 | A | 11/2000 | McAtee et al. | |
| 6,162,457 | A | 12/2000 | Martz | |
| 6,206,863 | B1 | 3/2001 | Skewes et al. | |
| 6,217,854 | B1 | 4/2001 | Farrell et al. | |
| 6,264,391 | B1 | 7/2001 | Kroha | |
| 6,322,801 | B1 | 11/2001 | Lorenzi et al. | |
| 6,328,811 | B1 | 12/2001 | Martin et al. | |
| 6,376,046 | B1 | 4/2002 | Hoshino et al. | |
| 6,391,835 | B1 | 5/2002 | Gott et al. | |
| 6,428,799 | B1 | 8/2002 | Cen et al. | |
| 6,467,981 | B1 | 10/2002 | Gueret | |
| 6,491,928 | B1 | 12/2002 | Smith, III | |
| 6,491,933 | B2* | 12/2002 | Lorenzi | A61Q 19/10 424/401 |
| 6,491,937 | B1 | 12/2002 | Slavtcheff et al. | |
| 6,509,304 | B1* | 1/2003 | Aoshima | A61K 8/02 424/401 |
| 6,547,468 | B2 | 4/2003 | Gruenbacher et al. | |
| 6,550,092 | B1 | 4/2003 | Brown et al. | |
| 6,607,739 | B1 | 8/2003 | Wallo | |
| 6,638,527 | B2 | 10/2003 | Gott et al. | |
| 6,645,611 | B2 | 11/2003 | Seth | |
| 6,656,487 | B2 | 12/2003 | Afriat et al. | |
| 6,730,317 | B2 | 5/2004 | Gueret | |
| 6,753,063 | B1 | 6/2004 | Pung et al. | |
| 6,783,294 | B2 | 8/2004 | Duden et al. | |
| 6,835,701 | B2 | 12/2004 | Seipel et al. | |
| 6,883,353 | B2 | 4/2005 | Goldoni et al. | |
| 6,878,380 | B2 | 5/2005 | Farrell et al. | |
| 6,902,338 | B2 | 6/2005 | Puvvada et al. | |
| 6,992,054 | B2 | 1/2006 | Lee et al. | |
| 7,033,964 | B2 | 4/2006 | Gillette | |
| 7,101,612 | B2 | 9/2006 | Lang et al. | |
| 7,115,535 | B1 | 10/2006 | Smith, III et al. | |
| 7,115,551 | B2 | 10/2006 | Hasenoehrl et al. | |
| 7,179,772 | B2 | 2/2007 | Keenan et al. | |
| 7,229,956 | B2 | 6/2007 | Bedford et al. | |
| 7,285,520 | B2 | 10/2007 | Krzysik et al. | |
| 7,288,513 | B2 | 10/2007 | Taylor et al. | |
| 7,350,256 | B2 | 4/2008 | Benjamin et al. | |
| 7,381,693 | B2 | 6/2008 | Keenan et al. | |
| 7,401,376 | B2 | 7/2008 | Benjamin et al. | |
| 7,419,321 | B2 | 9/2008 | Tereschouk | |
| 7,452,547 | B2 | 11/2008 | Lambino et al. | |
| 7,462,348 | B2 | 12/2008 | Gruenbacher et al. | |
| 7,490,382 | B2 | 2/2009 | Benjamin et al. | |
| 7,509,689 | B2 | 3/2009 | Reardon et al. | |
| 7,514,071 | B2 | 4/2009 | Simon et al. | |
| 7,581,273 | B2 | 9/2009 | Dobrin et al. | |
| 7,584,519 | B2 | 9/2009 | Ouellette et al. | |
| 7,589,053 | B2 | 9/2009 | Larsen et al. | |
| 7,614,812 | B2 | 11/2009 | Reddy et al. | |
| 7,647,667 | B2 | 1/2010 | Benjamin et al. | |
| 7,651,290 | B2 | 1/2010 | Bauer et al. | |
| 7,665,176 | B2 | 2/2010 | Benjamin et al. | |
| 7,674,058 | B2 | 3/2010 | Berger Sharp et al. | |
| 7,854,947 | B2 | 12/2010 | Cao et al. | |
| 7,874,756 | B2 | 1/2011 | Nuebel et al. | |
| 7,901,696 | B2 | 3/2011 | Eknoian et al. | |
| 8,137,018 | B2 | 3/2012 | Galvan-Nanez | |
| 8,157,464 | B2 | 4/2012 | Prax | |
| 8,186,853 | B2 | 5/2012 | Popovsky | |
| 8,308,388 | B2 | 11/2012 | Guay | |
| 8,475,817 | B2 | 7/2013 | Hasenoehrl et al. | |
| 8,501,642 | B2 | 8/2013 | Naruse et al. | |
| 8,534,947 | B2 | 9/2013 | Prax | |
| 8,546,640 | B2 | 10/2013 | Popovsky et al. | |
| 8,628,706 | B2* | 1/2014 | Glenn et al. | 264/50 |
| 8,987,187 | B2 | 3/2015 | Smets et al. | |
| 9,333,151 | B2 | 5/2016 | Smith, III et al. | |
| 2001/0003565 | A1 | 6/2001 | Mcosker et al. | |
| 2001/0018068 | A1* | 8/2001 | Lorenzi et al. | 424/443 |
| 2001/0028894 | A1 | 10/2001 | Gueret | |
| 2002/0098994 | A1 | 7/2002 | Zafar | |
| 2002/0178507 | A1 | 12/2002 | Goldoni et al. | |
| 2002/0192268 | A1 | 12/2002 | Alwattari et al. | |
| 2003/0024556 | A1 | 2/2003 | Guiramand et al. | |
| 2003/0079323 | A1 | 5/2003 | Ngai | |
| 2003/0143263 | A1 | 7/2003 | Durden et al. | |
| 2003/0180242 | A1 | 9/2003 | Eccard et al. | |
| 2003/0194425 | A1 | 10/2003 | Simon et al. | |
| 2003/0199404 | A1* | 10/2003 | Lorenzi et al. | 510/119 |
| 2003/0203010 | A1 | 10/2003 | Wallo | |
| 2003/0228352 | A1 | 12/2003 | Hasenoehrl et al. | |
| 2004/0116017 | A1 | 6/2004 | Smith, III et al. | |
| 2004/0147189 | A1 | 7/2004 | Smith, III et al. | |
| 2004/0170670 | A1 | 9/2004 | Smith et al. | |
| 2004/0175343 | A1 | 9/2004 | Osborne et al. | |
| 2004/0176002 | A1 | 9/2004 | Siegwart | |
| 2004/0237234 | A1 | 12/2004 | Young et al. | |
| 2004/0237235 | A1 | 12/2004 | Visioli et al. | |
| 2005/0000046 | A1 | 1/2005 | Popovsky et al. | |
| 2005/0065047 | A1* | 3/2005 | Shefer | A61K 8/11 510/141 |
| 2005/0125877 | A1 | 6/2005 | Benjamin et al. | |
| 2005/0129743 | A1 | 6/2005 | Benjamin et al. | |
| 2005/0148260 | A1 | 7/2005 | Kopacz et al. | |
| 2005/0202068 | A1 | 9/2005 | Hasenoehrl et al. | |
| 2006/0029625 | A1 | 2/2006 | Niebauer | |
| 2006/0144426 | A1 | 7/2006 | Mathews | |
| 2006/0246119 | A1 | 11/2006 | Eknoian et al. | |
| 2007/0071797 | A1 | 3/2007 | Hernandez-Munoa et al. | |
| 2007/0098659 | A1 | 5/2007 | Ip et al. | |
| 2007/0099813 | A1 | 5/2007 | Luizzi et al. | |
| 2007/0130706 | A1 | 6/2007 | Buhrow et al. | |
| 2007/0130707 | A1 | 6/2007 | Cohen et al. | |
| 2007/0271716 | A1 | 11/2007 | Spector | |

(56) References Cited

U.S. PATENT DOCUMENTS

| | | |
|---|---|---|
| 2007/0283516 A1 | 12/2007 | Rasmussen et al. |
| 2008/0104787 A1 | 5/2008 | Keenan et al. |
| 2008/0145388 A1 | 6/2008 | Roreger et al. |
| 2008/0152894 A1 | 6/2008 | Beihoffer et al. |
| 2008/0168748 A1 | 7/2008 | McCloskey |
| 2008/0247806 A1 | 10/2008 | Todd et al. |
| 2008/0299269 A1 | 12/2008 | Mane et al. |
| 2009/0081264 A1 | 3/2009 | Zabari |
| 2009/0178692 A1 | 7/2009 | Warr et al. |
| 2009/0286437 A1 | 11/2009 | Cunningham et al. |
| 2010/0130988 A1 | 5/2010 | Bolton |
| 2011/0017617 A1 | 1/2011 | Findlay et al. |
| 2011/0167576 A1 | 7/2011 | Muhammad |
| 2012/0028869 A1 | 2/2012 | Crawford et al. |
| 2012/0246851 A1 | 10/2012 | Smith, III et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2015/0000057 A1 | 1/2015 | McConaughy et al. |
| 2015/0000059 A1 | 1/2015 | McConaughy et al. |
| 2015/0005221 A1 | 1/2015 | McConaughy et al. |
| 2015/0005223 A1 | 1/2015 | McConaughy et al. |
| 2015/0141310 A1 | 5/2015 | Smets et al. |
| 2016/0324732 A1 | 11/2016 | Smith, III et al. |
| 2017/0079484 A1 | 3/2017 | Smith, III et al. |
| 2017/0096625 A1 | 4/2017 | McConaughy et al. |
| 2017/0151132 A1 | 6/2017 | Smith, III et al. |

FOREIGN PATENT DOCUMENTS

| | | |
|---|---|---|
| CN | 2900535 Y | 5/2007 |
| CN | 201230858 Y | 5/2009 |
| CN | 201501856 U | 6/2010 |
| CN | 201574146 U | 9/2010 |
| CN | 202168784 U | 3/2012 |
| DE | 197 45 964 A1 | 6/1998 |
| DE | 19744213 | 4/1999 |
| DE | 20017205 | 12/2000 |
| DE | 202 17 888 U1 | 5/2003 |
| DE | 20304298 | 6/2003 |
| DE | 10301838 | 7/2004 |
| DE | 202004007851 | 8/2004 |
| DE | 20 2008 016 104 U1 | 11/2011 |
| EP | 0032793 B1 | 3/1984 |
| EP | 0047116 B1 | 7/1985 |
| EP | 0272492 A2 | 6/1988 |
| EP | 387693 | 9/1990 |
| EP | 387694 | 9/1990 |
| EP | 0 863 201 A2 | 9/1998 |
| EP | 1000605 A2 | 5/2000 |
| EP | 1 090 627 A1 | 4/2001 |
| EP | 1 153 554 A1 | 11/2001 |
| EP | 1 102 577 B1 | 9/2002 |
| EP | 1 393 717 A1 | 3/2004 |
| EP | 2 177 207 A2 | 4/2010 |
| EP | 2 236 067 A1 | 10/2010 |
| EP | 2 468 235 A1 | 6/2012 |
| FR | 2 694 877 B1 | 10/1994 |
| FR | 2 725 145 A1 | 4/1996 |
| FR | 2 752 375 A1 | 2/1998 |
| FR | 2822045 | 9/2002 |
| FR | 2855741 | 12/2004 |
| GB | 2163947 A | 3/1986 |
| GB | 2222526 A | 3/1990 |
| JP | 02265516 | 10/1990 |
| JP | 08084684 | 4/1996 |
| JP | 09299271 | 11/1997 |
| JP | 10000170 | 1/1998 |
| JP | 10137152 A | 5/1998 |
| JP | 2000-166800 A | 6/2000 |
| JP | 2000-256180 A | 9/2000 |
| JP | 2002142857 | 5/2002 |
| JP | 2002275031 | 9/2002 |
| JP | 2002315689 | 10/2002 |
| JP | 2003-192530 A | 7/2003 |
| JP | 2004016560 | 1/2004 |
| JP | 2004-238319 A | 8/2004 |
| JP | 2004236996 | 8/2004 |
| JP | 2005-168751 A | 6/2005 |
| JP | 2006082263 | 3/2006 |
| JP | 2006130194 | 5/2006 |
| JP | 2007-289377 A | 11/2007 |
| JP | 3143919 U | 8/2008 |
| JP | 2009292750 | 12/2009 |
| JP | 2010-37199 A | 2/2010 |
| JP | 2010046129 | 3/2010 |
| JP | 2011-24895 A | 2/2011 |
| KR | 2010-0000279 A | 1/2010 |
| KR | 2010-0015042 A | 2/2010 |
| KR | 2012-0057773 A | 6/2012 |
| SE | 8703015 | 2/1989 |
| WO | 94/12088 A1 | 6/1994 |
| WO | 97/04683 | 2/1997 |
| WO | 97/45256 A1 | 12/1997 |
| WO | 99/53896 A1 | 10/1999 |
| WO | 01/08655 A1 | 2/2001 |
| WO | 01/08658 A1 | 2/2001 |
| WO | 02/091895 A1 | 11/2002 |
| WO | 03/042251 A1 | 5/2003 |
| WO | 03/043481 A2 | 5/2003 |
| WO | 03/053397 A1 | 7/2003 |
| WO | 03/061607 A1 | 7/2003 |
| WO | 2004/000235 A2 | 12/2003 |
| WO | 2004/019867 A2 | 3/2004 |
| WO | 2007/027711 A1 | 3/2007 |
| WO | 2007/054853 A1 | 5/2007 |
| WO | 2007/085428 A2 | 8/2007 |
| WO | 2007/124342 A2 | 11/2007 |
| WO | 2007/135583 A2 | 11/2007 |
| WO | 2007/146103 A2 | 12/2007 |
| WO | 2008/081055 A1 | 7/2008 |
| WO | 2008/086588 A1 | 7/2008 |
| WO | 2008/096966 A1 | 8/2008 |
| WO | 2008/113973 A1 | 9/2008 |
| WO | 2008/116147 A2 | 9/2008 |
| WO | 2009/125410 A2 | 10/2009 |
| WO | 2010/058272 A2 | 5/2010 |
| WO | 2010/130816 A1 | 11/2010 |
| WO | 2011/100660 A1 | 8/2011 |
| WO | 2012/084427 A1 | 6/2012 |
| WO | 2012/084649 A1 | 6/2012 |
| WO | 2012/093102 A1 | 7/2012 |

* cited by examiner

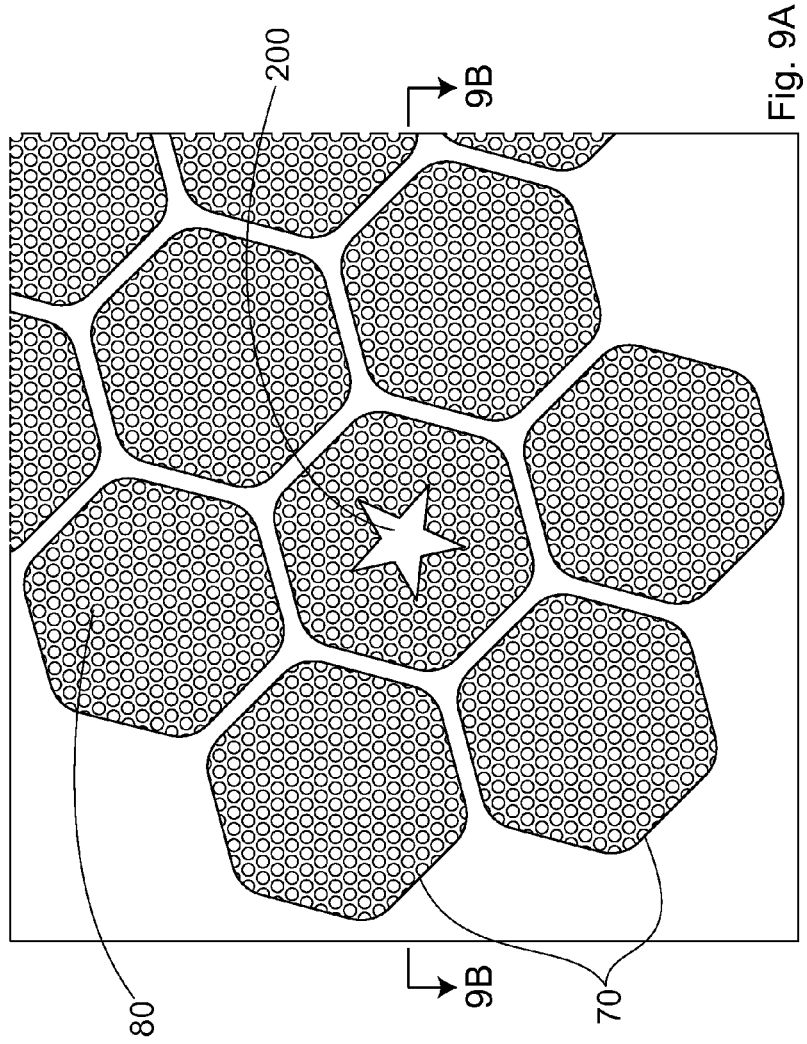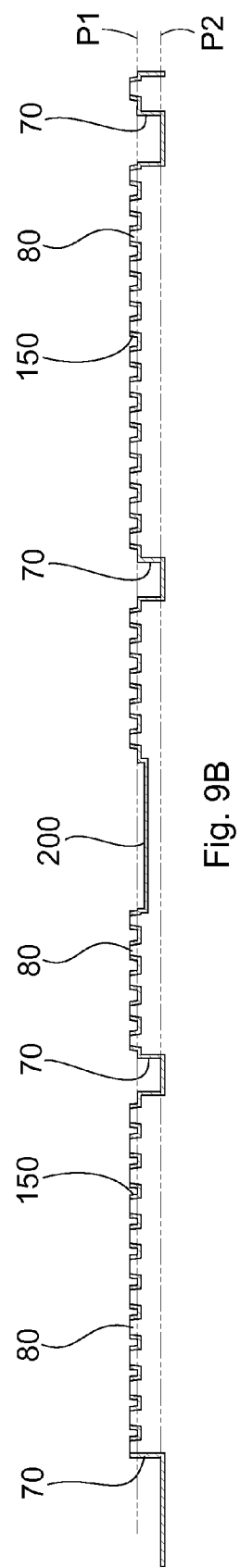

PERSONAL CARE COMPOSITIONS AND ARTICLES

FIELD

The present application is directed to personal care compositions and articles.

BACKGROUND

Cleansing is an activity that has been done for many years. Over time, cleansing has involved the use of compositions such as bar and liquid soaps, body washes, shampoos, conditioners, liquid and/or solid detergents, and the like. For these compositions, consumers desire good cleansing properties and lathering characteristics, mildness toward the target surface, like skin, fabric, or hard surface, and the ability to provide benefit agents to the target surface.

Some cleansing has been done with rigid cleansing compositions, like bar soap. These rigid forms can be difficult for the consumer to handle, especially when wet. Also, they are difficult to use directly on the target area for cleansing as the contact surface area of the bar soap is limited by the shape of the target surface.

To enhance a consumer's experience, such cleansing compositions can also be coupled with implements such as a washcloth, a sponge, or a puff. For example, many consumers dispense liquid soaps or body washes onto a puff and then cleanse by applying the puff to their skin and/or hair. Similarly, many consumers rub bar soaps with a washcloth and then cleanse by applying the washcloth to their skin and/or hair. Additionally, many consumers apply cleansing compositions to sponges to clean hard surfaces.

Although a consumer's experience with a cleansing composition can be enhanced by coupling the cleansing composition with an implement, to date, such an experience has not been completely ideal. For example, coupling such cleansing compositions with an implement tends to lead to clutter in the kitchen, shower, or bath as a consumer needs to carry or store cumbersome bottles, bars, jars, and/or tubes of cleansing products and implements. Additionally, coupling requires the user to perform additional steps like applying the body wash or soap on the implement and then rubbing or wiping the implement on the target surface rather than just applying the body wash and/or soap directly to the target surface. As such, more water tends to be consumed increasing the waste and carbon footprint of the consumer.

Further, certain personal cleansing compositions, such as bar soaps, can have difficulty providing the consumer with the desired deposition of benefit agents, even when coupled with an implement. Some attempts have been made to combine an implement with a personal cleansing composition in a personal care article. However, these executions were not ideal. For example, one such article included a non-compliant bar soap coupled with an implement. The rigidity of this type of execution does not conform to the surface to which it is applied making it difficult to thoroughly clean the target surface.

Accordingly, it would be desirable to provide a compliant personal care composition and or article having desirable cleansing properties, including suitable lathering and rinsing characteristics.

SUMMARY

A compliant personal care composition, comprising: a) from about 20% to about 80%, by weight of the composition, of a surfactant; b) from about 3% to about 40%, by weight of the composition, of a water insoluble hygroscopic fiber, fine, or filament; and c) a solvent; wherein the composition has a compliance value of about 0.01 kg/mm to about 1.5 kg/mm before a simulated use.

A compliant personal care article, comprising: a) a composition comprising: i) from about 20% to about 80%, by weight of the composition, of a surfactant; ii) from about 3% to about 40%, by weight of the composition, of a water insoluble hygroscopic filament comprising a fiber and a fine; and iii) a solvent; and b) a water insoluble substrate; wherein the composition is at least partially surrounded by the substrate and the article has a compliance value of about 0.01 kg/mm to about 1.5 kg/mm before a simulated use.

A compliant personal cleansing article, comprising: a) from about 40% to about 99.6%, by weight of the article, of a cleansing composition comprising: i) from about 20% to about 80%, by weight of the composition, of a surfactant; ii) from about 3% to about 40%, by weight of the composition, of a fine, fiber, or filament, comprising cellulose; and iii) a solvent; and b) a multiplanar film at least partially surrounding the composition; wherein the article has a compliance value of about 0.01 kg/mm to about 1.5 kg/mm before a simulated use.

BRIEF DESCRIPTION OF THE DRAWINGS

FIG. 9A is a top perspective view of another exemplary substrate;

FIG. 9B is a cross sectional view of the exemplary substrate of FIG. 9A, along line 9B-9B;

DETAILED DESCRIPTION OF THE INVENTION

Figure 1:
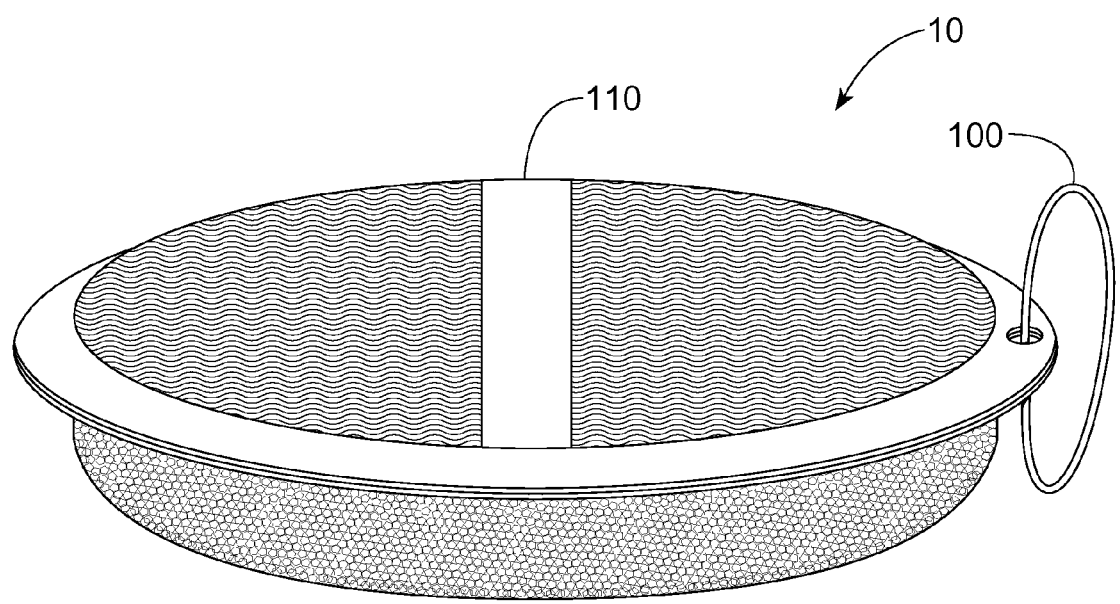
FIG. 1 depicts a perspective view of an example of a personal care article.

This application claims the benefit of U.S. Provisional Application Ser. Nos. 61/840,084; 61/840,157; 61/918,739, 61/840,120, 61/886,502, and 61/886,508, the entirety of which are incorporated by reference herein.

As used herein, the following terms shall have the meaning specified thereafter:

"Cellulose" as used herein refers to cellulose in the form of fines, fibers, and/or filaments; and/or aggregates thereof.

"Compliant" as used herein refers to an article and/or composition with a compliance value of about 1.5 kg/mm or less as measured according to the Compliance Test set out below.

"Fiber" as used herein refers to an elongate particulate having an apparent length exceeding its apparent diameter, i.e. a length to diameter ratio of about 7 or more. Fibers having a non-circular cross-section and/or tubular shape are common; the "diameter" in this case may be considered to be the diameter of a circle having cross-sectional area equal to the cross sectional area of the fiber. "Fiber length", "average fiber length" and "weighted average fiber length", are terms used interchangeably herein all intended to represent the "Length Weighted Average Fiber Length". Fiber length and diameter can be measured in accordance with standard procedures and machinery, like a STFI FiberMaster available from Innventia AB, Sweden. The recommended method for measuring fiber length using this instrument is essentially the same as detailed by the manufacturer of the Fiber Master in its operation manual.

"Filament" as used herein refers to a combination of fibers and fines.

"Fine" as used herein refers to both primary and secondary fines (unless otherwise noted) which are water insoluble materials that pass through a 200 mesh screen under conditions defined in the TAPPI method T-261(80).

"g/use" refers to grams per use, which is the unit used for rate of consumption. The method for measuring and/or calculating the rate of consumption is described herein.

"Land" area is a generally flattened area existing within a plane and is generally impermeable, existing pores in that area are usually sealed off in the manufacturing process. While the land area is generally flat, there is no requirement that it be perfectly flat and it could itself contain some patterning. Patterning could include, for example, creating roughness in order to reduce the gloss of the substrate.

"Natural" as used herein refers to materials that can be derived from plants, animals, or insects, or materials that can be byproducts of plants, animals, or insects; excluding materials produced by bacteria.

"Personal care" refers to a composition or article for topical application to skin and/or hair. Personal care compositions can be rinse-off formulations, in which the composition can be applied topically to the skin and/or hair and then subsequently rinsed within seconds to minutes of application. The composition could also be wiped off using a substrate.

"Pores" are holes in a substrate to allow passage of components such as water or other fluids, air or other gases and vapors, and/or material components such as surfactant or actives which may be dissolved or suspended in fluids.

"Reusable" refers to an article that can be used for a number of usage events, such as showers and/or baths, wherein the number of usage events can be about 5 or greater, about 7 or greater, about 10 or greater, about 15 or greater, about 20 or greater, about 25 or greater, or about 30 or greater.

"Simulated use" as used herein, refers to a simulated use as described in the Compliance Test below for measuring compliance after a simulated bath/shower, unless otherwise noted.

"Soft solid" as used herein refers to a compositional form which is viscoelastic, like a dough or a paste, and generally remains together as a single piece during use.

"Surface aberration" refers to a raised portion on a surface of a substrate which can be readily apparent to the naked eye and can form a pattern or design on a surface of a substrate. A surface aberration is not a pore or a protuberance.

"Unit cell" is a repeating geometrical pattern which can be measured along with the dimensions of the land and raised areas or structures within it in order to calculate the fractional amounts of land and raised areas for the substrate. A unit cell can be made up of, for example, surface aberrations, land area, and/or features.

"Usage event" refers to one cycle of the Consumption Test described below.

"Water insoluble" when used in relation to fines, fibers, or filaments, refers to those that do not substantially dissolve when placed in water at 42° C. for 15 minutes.

"Water insoluble substrate" refers to a substrate which does not dissolve before at least 10 simulated uses.

"Water penetrable substrate" refers to a substrate which allows water to pass through it into the personal care article and/or to the composition.

Personal Care Compositions

Personal care compositions come in many forms. One of the more common forms is bar soap. Bar soap is generally non-compliant and rigid. The rigidity of most bar soaps make them difficult to grip making it more difficult to use during cleansing. Rigid bar soaps also have the disadvantage in that only the small part of the surface which directly contacts the skin can be used for cleansing and this surface area is limited by the bar's non-compliant nature. Conventional rigid bar soap has a compliance value of about 2.5 kg/mm or above.

On the other hand, compliant personal care compositions can bend to some degree to more fully contact the target surface, like the body. This can allow for easier handling of the composition by the consumer and more efficient cleansing. For example, if a compliant personal care composition is originally flat with no curve, when applied to an arm for cleansing there would be some amount of bend to better fit to the arm. Likewise, if the composition's shape has a small amount of a curve, when applied to the arm the composition would bend to some degree to more fully contact the arm. Oppositely, if the original personal care composition is curved such that it would not need to bend to fit to a curved surface like the arm, then it would bend to straighten when applied to a less curved surface like an abdomen.

A challenge when trying to formulate compliant personal care compositions is first formulating for the right amount of compliance. The compositions need to be able to be manipulated by the user with an acceptable amount of effort. This acceptable level of compliance was found to be from about 0.01 kg/mm to about 1.5 kg/mm. Additional examples of suitable compliance values include from about 0.03 kg/mm to about 1.0 kg/mm; about 0.10 kg/mm to about 0.75 mm/kg; about 0.10 kg/mm to about 0.6 kg/mm; about 0.05 kg/mm to about 0.5 kg/mm; or about 0.10 kg/mm to about 0.30 kg/mm.

Another challenge when formulating compliant compositions is the ability to maintain an acceptable compliance through the life of the composition. As some reusable compliant personal care compositions/articles experience repeated wetting and then drying processes, the compositions can become hard or rigid, see Comparative Example C1 (below) which has a compliance before a simulated use of 0.52 kg/mm and 30 minutes after one simulated use of 0.32 kg/mm, but at 50.5 hours after the one simulated use the compliance value reaches 1.63 kg/mm. Thus, the benefits of a compliant composition can be lost after only a single or a few uses resulting in consumer dissatisfaction. Without being limited by theory, this is believed to at least be caused in part by the loss of moisture from the composition which can cause the composition to crack into domains as it dries. This cracking exposes the interior to even more rapid water loss which only exacerbates the problem over time.

One way of looking at whether a composition or article can likely maintain its compliance through the life of an article is to see whether the composition or article has an acceptable compliance level, as noted above, after repeated simulated uses. For example, the composition or article can have an acceptable compliance, after 10 simulated uses, 12 simulated uses, 15 simulated uses, 20 simulated uses, or 25 simulated uses. In one example, the composition or article can have a compliance value of 0.01 kg/mm to about 1.5 kg/mm after 12 hours of drying after 15 simulated uses. In another example, the composition or article can have a compliance value of about 0.10 kg/mm to about 0.75 kg/mm after drying for 12 hours after 10 simulated uses.

In addition, another factor to consider when developing an acceptable composition or article is its compliance after a long period of non-use. Some compositions or articles can lose their compliance after long periods with no exposure to water, so it can be helpful to also look at whether a composition or article has an acceptable compliance level when measured 48 hours after the last use.

One solution to these problems has surprisingly been the use of hygroscopic filaments in the composition. Hygroscopic filaments are made of fibers and fines. Without wishing to be limited by theory, it is believed the fibers and fines can work together to form a network. This is believed to be contributed to, in part, by the length and aspect ratio of the fibers. The ability to form a network may be an important feature in order to minimize the common tendency of materials to crack when they lose solvent (water drying). Solvent loss causes dimensional changes with materials due to the loss of solvent volume. The composition tends to therefore shrink, crack, or change its density. Shrinking and cracking are common in coatings when solvent is lost, the result of the internal stress created as the solvent volume is lost. It is more desirable for a composition to shrink (which is a flow, or it acts as a viscous material to relax the stress) instead of crack (which is an elastic behavior, not a flow). Cracking opens up fissures allowing even faster solvent loss throughout the composition. Without wishing to be limited by theory, we believe the filament may not allow cracking to occur due to long range order, i.e., network behavior.

The aspect ratio of a fiber describes the relationship between the length and diameter of the fiber and is calculated by dividing end to end length by diameter. Aspect ratios acceptable for fibers used herein can include those above about 9, above about 9.5, above about 10, above about 100, above about 1000, above about 10,000, to about 100, to about 500, to about 1000, to about 10,0000, to about 100,000, to about 300,000, or any combination thereof.

It is also believed that the hygroscopic water insoluble nature of filaments can further contribute to maintaining compliance upon repeated use. Hygroscopic filaments are water loving or hydrophilic by chemistry so may help to retain water in the composition. Additionally, by being water insoluble, certain filaments can remain in the composition even after exposure to water enabling them to continue contributing the properties of the composition through multiple uses instead of dissolving away. Other filaments may partially or fully dissolve during use enabling them to provide order to the composition and provide soluble components that may help plasticize the composition. It may be beneficial for filaments or portions of the filaments to exit an article during use. For example, filaments may exit the article through pores in the substrate and this may work to enhance scrubbing or to give the appearance the article is being depleted as the composition is used over time.

Another property that can have an impact on granular compositions is the angle of repose. The angle of repose is a measure of the flow ability of the particles in a granular composition and can impact processing of a granular composition. The angle of repose can be, for example, less than about 60° as measured by ASTM D6393.

Personal care compositions can be in the form of a soft solid. Personal care compositions can comprise a surfactant; and a hygroscopic fine, a hygroscopic fiber, or a combination thereof (i.e. a hygroscopic filament). The composition can include, for example, from about 1% to about 99.5%, or from about 10% to about 70%, or from about 20% to about 80%, or from about 20% to about 50%, by weight of the composition, of a surfactant or a mixture of surfactants. A surfactant can be, for example, in the form of a solid powder.

Suitable synthetic surfactants for a personal care composition include, for example, sulfates, sulfonates, alkyl sulfates, linear alkyl sulfates, branched alkyl sulfates, linear alkyl ether sulfates, branched alkyl ether sulfates, linear alkyl sulfonates, branched alkyl sulfonates, linear alkyl ether sulfonates, branched alkyl ether sulfonates, alkyl aromatic sulfates, alkyl aromatic sulfonates, isethionates, cocoamide monoethanolamine, cocoamidopropyl betaine, glucosides, decyl glucoside, lauryl glucoside, or a combination thereof.

Some additional suitable synthetic surfactants include, for example, anionic, nonionic, cationic, zwitterionic, amphoteric surfactants, or combinations thereof. For example, the synthetic surfactant can comprise an anionic surfactant. The anionic surfactant can be branched or linear. Examples of suitable linear anionic surfactants include ammonium lauryl sulfate, ammonium laureth sulfate, sodium lauryl sulfate, sodium laureth sulfate, potassium laureth sulfate, sodium lauryl sarcosinate, sodium lauroyl sarcosinate, sodium lauroyl isethionate, sodium cocoyl isethionate, lauryl sarcosine, cocoyl sarcosine, ammonium cocoyl sulfate, potassium lauryl sulfate, or combinations thereof.

The synthetic surfactant can also comprise sodium laureth (n) sulfate, hereinafter SLEnS, and/or sodium trideceth(n) sulfate, hereinafter STnS, where n defines the average moles of ethoxylation. The n for the SLEnS and/or the STnS can range from about 0 to about 8, from about 1 to about 3, about 2, or about 1. It will be understood that a material such as SLEnS or STnS can comprise a significant amount of molecules having no ethoxylate, 1 mole ethoxylate, 2 mole ethoxylate, 3 mole ethoxylate, and so on in a distribution which can be broad, narrow, or truncated. For example, SLE1S can comprise a significant amount of molecules which have no ethoxylate, 1 mole ethoxylate, 2 mole ethoxylate, 3 mole ethoxylate, and so on in a distribution which can be broad, narrow, or truncated and still comprise SLE1S where an average distribution can be about 1. Similarly, ST2S can comprise a significant amount of molecules which have no ethoxylate, 1 mole ethoxylate, 2 mole ethoxylate, 3 mole ethoxylate, and so on in a distribution which can be broad, narrow, or truncated and still comprise ST2S, where an average distribution can be about 2.

The synthetic surfactant can also comprise one or more branched anionic surfactants and monomethyl branched anionic surfactants such as sodium trideceth sulfate, sodium tridecyl sulfate, sodium C12-13 alkyl sulfate, C12-13 pareth sulfate, sodium C12-13 pareth-n sulfate, or combinations thereof.

As described above, the synthetic surfactant can comprise a nonionic surfactant. Nonionic surfactants for use in the composition can include, for example, those selected from the group consisting of alkyl glucosides, alkyl polyglucosides, polyhydroxy fatty acid amides, alkoxylated fatty acid esters, sucrose esters, amine oxides, or mixtures thereof.

The synthetic surfactant can also comprise a cationic surfactant. Cationic surfactants for use in a composition include, but are not limited to, fatty amines, di-fatty quaternary amines, tri-fatty quaternary amines, imidazolinium quaternary amines, or combinations thereof.

The synthetic surfactant can also comprise an amphoteric surfactant. Suitable amphoteric surfactants can include those that are broadly described as derivatives of aliphatic secondary and tertiary amines, in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition can include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. The surfactant included in the personal care composition can comprise, for example, an amphoteric surfactant that can be selected from the group consisting of sodium lauroamphoacetate, sodium cocoamphoacetate, disodium lauroamphoacetate disodium cocodiamphoacetate, and mixtures thereof.

The synthetic surfactant can also comprise a zwitterionic surfactant. Suitable zwitterionic surfactants can include, for example, those that are broadly described as derivatives of aliphatic quaternary ammonium, phosphonium, and sulfonium compounds, in which the aliphatic radicals can be straight or branched chain, and wherein one aliphatic substituent contains from about 8 to about 18 carbon atoms and one contains an anionic group, e.g., carboxy, sulfonate, sulfate, phosphate, or phosphonate. In one example, the zwitterionic surfactant included in the composition can comprise one or more betaines such as cocoamidopropyl betaine.

The surfactant may also comprise a soap. The composition can include, for example, from about 20% to about 99.5%, from about 20% to about 75%, from about 20% to about 50%, or any combination thereof, by weight of the composition, of a soap.

The soap can include, for example, alkali metal or alkanol ammonium salts of alkane- or alkene monocarboxylic acids. Sodium, magnesium, potassium, calcium, mono-, di- and tri-ethanol ammonium cations, or combinations thereof, can be suitable. In one example, the soap comprises a sodium soap. In another example, the soap comprises a sodium soap and from about 1% to about 25% of at least one of ammonium, potassium, magnesium, and calcium soap. Suitable soaps can also include the well-known alkali metal salts of alkanoic or alkenoic acids having from about 12 to 22 carbon atoms, from about 12 to about 18 carbon atoms; or alkali metal carboxylates of alkyl or alkene hydrocarbons having from about 12 to about 22 carbon atoms.

The composition can also include soaps having a fatty acid distribution of coconut oil that can provide a lower end of a broad molecular weight range or a fatty acid distribution of peanut or rapeseed oil, or their hydrogenated derivatives, which can provide an upper end of the broad molecular weight range.

A soap in the composition can also include, for example, a fatty acid distribution of tallow and/or vegetable oil. The tallow can include fatty acid mixtures that typically have an approximate carbon chain length distribution of 2.5% C14, 29% C16, 23% C18, 2% palmitoleic, 41.5% oleic, and 3% linoleic. The tallow can also include other mixtures with similar distribution, such as the fatty acids derived from various animal tallows and/or lard. According to one example, the tallow can also be hardened (i.e., hydrogenated) to convert part or all of the unsaturated fatty acid moieties to saturated fatty acid moieties.

Suitable vegetable oil can be selected, for example, from the group consisting of palm oil, coconut oil, palm kernel oil, palm oil stearine, and hydrogenated rice bran oil, and mixtures thereof. In one example, the vegetable oil is selected from the group consisting of palm oil stearine, palm kernel oil, coconut oil, and combinations thereof. Suitable coconut oil can include a proportion of fatty acids having 12 carbon atoms or more of about 85%. Such a proportion can be greater when mixtures of coconut oil and fats such as tallow, palm oil, or non-tropical nut oils or fats are used where the principle chain lengths can be C16 and higher. According to one example, the soap included in the composition can be a sodium soap having a mixture of about 67-68% tallow, about 16-17 coconut oil, and about 2% glycerin, and about 14% water.

Soap is often made by a classic kettle boiling process or modern continuous soap manufacturing processes wherein natural fats and oils such as tallow or coconut oil or their equivalents can be saponified with an alkali metal hydroxide using procedures well known to those skilled in the art. Alternatively, the soaps can be made by neutralizing fatty acids such as lauric (C12), myristic (C14), palmitic (C16), or stearic (C18) acids with an alkali metal hydroxide or carbonate.

The personal care composition also comprises a hygroscopic fine, hygroscopic fiber, or a hygroscopic filament. The composition can contain from about 3% to about 40%, by weight of the composition, of the fine, fiber, or filament. Additional acceptable levels can include from about 5% to about 35%, from about 10% to about 30%, or from about 15% to about 25%, by weight of the composition. A filament comprises fibers and fines. A filament can comprise from about 1% to about 95%, by weight of the filament, of fines, and from about 99% to about 5%, by weight of the filament, of fibers; or from about 20% to about 90%, by weight of the filament, of fines, and from about 80% to about 10%, by weight of the filament, of fibers; or from about 50% to about 70%, by weight of the filament, of fines, and from about 50% to about 30%, by weight of the filament, of fibers. A filament may comprise a single type of fiber or multiple types of fibers. A filament may likewise comprise a single type of fine or multiple types of fines.

A fine, fiber, or filament may be, for example, natural, like from a plant or animal, modified natural, or a combination thereof. Examples of animal fines, fibers, or filaments may include wool, silk, and mixtures thereof. Plant fines, fibers, or filaments may, for example, be derived from a plant like wood, bark, oat, corn, cotton, cotton linters, flax, sisal, abaca, hemp, hesperaloe, jute, bamboo, bagasse, kudzu, corn, sorghum, gourd, agave, loofah, or mixtures thereof.

One further example of a plant fine, fiber, or filament is a cellulose fine, fiber, or filament. Another exemplary fine, fiber, or filament comprises a regenerated cellulose, like rayon.

Wood pulp fines, fibers, or filaments may include, for example, hardwood pulp or softwood pulp. Non-limiting examples of hardwood pulp filaments include filaments derived from a fiber source selected from the group consisting of: *Acacia, Eucalyptus*, Maple, Oak, Aspen, Birch, Cottonwood, Alder, Ash, Cherry, Elm, Hickory, Poplar, Gum, Walnut, Locust, Sycamore, Beech, *Catalpa, Sassafras, Gmelina, Albizia, Anthocephalus*, and *Magnolia*. Non-limiting examples of softwood filaments include filaments derived from a fiber source selected from the group consisting of: Pine, Spruce, Fir, Tamarack, Hemlock, Cypress, and Cedar.

A fine, fiber, or filament may also be synthetic. Some examples of suitable synthetic hygroscopic fibers, fines, or filaments include nylon, polyester, polyvinyl alcohol, starch, starch derivatives, pectin, chitin, chitosan, cellulose derivatives such as methylcellulose, hydroxypropylcellulose, alkoxy celluloses, or a combination thereof.

The fibers will have a length and diameter. The fibers may have a length weighted average of about 6 cm or less, about 5 cm or less, about 2 cm or less, about 1 cm or less, about 8 mm or less, about 6 mm or less, about 4 mm or less, about 3 mm or less, about 2 mm or less, or about 1 mm or less. The fibers may have an average diameter of about 15 µm, about 20 µm, to about 35 µm, to about 40 µm, or any combination thereof. Fiber length can be used to help determine whether a particular fiber will require more energy to be mixed into a composition. For example, fiber lengths of greater than 1.0 mm were found to require more energy than desired to mix into a composition. Thus, fiber length values of less than 1.0 mm can be used where lower levels of energy are desired to incorporate the fiber into a composition.

The fibers may also have a kink angle. Fiber "kink" is a measurement of an abrupt change in the curvature of a fiber and is defined by the modified Kibblewhite's Kink Index. The angle of this abrupt change is defined as the "kink angle". Kink angle will affect the volume one fiber can occupy, essentially a fiber with a higher kink angle will occupy greater volume filling space more efficiently, this will affect the level of fiber needed to meet the desired compliance value. Exemplary fibers for use herein can have a kink angle or about 35 to about 65, about 40 to about 60, about 45 to about 55, or any combination thereof.

Another property of fibers is the shape factor. The shape factor describes the ratio of the fiber end to end distance as projected in space and the fiber length as measured along the fiber. For instance, a straight fiber will have a high shape factor, since the end to end distance approaches the value of the length along the fiber, while a curly fiber will have a low shape factor. Exemplary fibers for use herein can have a shape factor of about 70 to about 95.

One more property of a fiber is the curl value. The curl value describes the degree of non-straightness of a fiber. The STFI FiberMaster uses the following equation to calculate curl values: Curl value=[(100/Shape Factor)−1]*100. Exemplary fibers for use herein can have a curl value of about 10 to about 25.

Fines have a greater surface area and are able to retain more solvent than higher aspect ratio fibers. Thus, fines can be used to help tune the composition or article to the desired compliance value. Fines can also be useful in formulating a composition that will be used up over time. Fines that are smaller than the opening in a substrate can be separated from the composition during use and exit the article through the substrate openings allowing the composition to become smaller during use and helping to signal the end of the life of the composition or article.

Fines may include both primary and secondary fines. Primary fines are naturally produced by the plant or animal source. Secondary fines are derived from fibers, meaning they start as fibers and then are processed into smaller pieces. Secondary fines may be derived, for example, from a natural fiber, like a plant fiber or animal fiber, a modified natural fiber, or a combination thereof. The fiber sources listed above are suitable for their primary fines or for their fibers to be converted into secondary fines and used herein. For example, a fine may comprise cellulose.

Some exemplary cellulose filaments and some of their properties and the properties of the included fibers are below:

| Water insoluble, natural filament | Fiber Length (mm) | Fiber Width (um) | Fiber Shape Factor | Fiber Curl Value | Fiber Kink Angle (deg) | Fiber Kink/mm | Fiber Aspect ratio | Britt Jar Fines (%) |
|---|---|---|---|---|---|---|---|---|
| Example HG1 | 2.776 | 33.5 | 84.5 | 18.3 | 55.79 | 0.29 | 82.9 | <3 |
| Example HG2 | 1.224 | 21.8 | 87.7 | 14.0 | 50.66 | 0.51 | 56.1 | ~20 |
| Example HG3 | 0.760 | 33.1 | 89.7 | 11.5 | 48.73 | 0.48 | 23.0 | 26.2 |
| Example HG4 | 0.403 | 28.4 | 84.7 | 18.1 | 54.56 | 0.95 | 14.2 | 54.3 |
| Example HG5 | 0.350 | 24.9 | 81.6 | 22.5 | 51.75 | 1.03 | 14.1 | 72.3 |
| Example HG6 | 0.287 | 29.5 | 80.5 | 24.2 | 49.59 | 1.23 | 9.7 | 88.6 |

An analysis of the impact of filament properties on the compliance 50.5 hrs after use was conducted using compliance values for examples D7-D10 (below) and the corresponding properties of the corresponding filament examples HG3-HG6. These examples were selected for analysis of filament and compliance structure property relationships since other composition variables were maintained constant.

The analysis indicates that for a fixed wt % of filament in the composition (20% for these examples), filament characteristics like % fines, aspect ratio, length, kink/mm, shape factor, and curl value can be used to modify the compliance of an article 50.5 hrs after use. Thus, the selection of filament properties can be used to enable a broader range of surfactant systems and concentrations to maintain desired compliant properties. For instance, surfactants with a higher crystallinity have a tendency to have a more rigid structure when in a dried composition. This tendency, however, can combated by selecting a filament with properties that tend to help lower compliance of a composition. These properties are shown in a regression model in FIGS. 10-15.

So, as shown in the regression models, selection of a filament with any of the following properties: lower aspect ratio, shorter length, higher fines %, greater number of kinks/mm, greater shape factor, and/or greater curl value, has a tendency to give a lower compliance composition. Thus, a more crystalline surfactant system could be paired with a filament having one or a combination of those properties in order to balance the more rigid nature of the surfactant system and arrive at an acceptable compliance after drying. Conversely, a less crystalline surfactant system could be paired with filaments having any of the following: higher aspect ratio, longer length, lower fines %, lower number of kinks/mm, lower shape factor, and/or lower curl value, to balance the more fluid nature of this type of surfactant system to arrive at an acceptable compliance after drying.

Certain advantages and disadvantages are present with filament property selection. For example, the use of a filament with shorter fibers and a high fines content enables facile mixing with the surfactant system, however examples D6-D14 indicate that a higher wt % of such filaments may be needed to achieve a desired compliance. Conversely, filaments comprised of longer fibers and a lower wt % of fines can achieve desired compliance values at lower wt % in the composition. However, filaments with longer fibers and lower fines % are more difficult to process and require more energy to mix with surfactant systems. Thus, these properties can also be considered when formulating a personal care composition.

The composition may also comprise a solvent. Solvents for use herein can include, for example, water glycerin, dipropylene glycol, soybean oil, sucrose polyesters, or combinations thereof. Solvent can be present, for example, in an amount of about 5% to about 50%, about 10% to about 45%, about 15% to about 40%, about 20% to about 35%, or any combination thereof, by weight of the composition.

The composition disclosed herein can also include one or more additional ingredients such as polymers, gums, pluronics, inorganic salts such as zinc carbonate, antimicrobial agents such as zinc pyrithione, actives, brighteners, silica, moisturizers or benefit agents, and emulsifiers.

The composition will also have a consumption rate as measured by the Consumption Test. The composition may have a consumption, for example, of about 0.25 g to about 14 g per use; about 0.5 g to about 8 g per use; about 0.5 g to about 7 g per use; or about 0.5 g to about 6 g per use.

Personal Care Articles

The above described personal care compositions may also be part of a personal care article. A personal care article comprises a substrate and a personal care composition. A personal care article may contain from about 40% to about 99.6%, by weight of the article, of a personal care composition. Additional acceptable ranges of composition include from about 50% to about 99% or from about 75% to about 98%, by weight of the article. A substrate may at least partially surround a composition or it may surround a composition. The personal care article may also comprise multiple substrates. A substrate may be adjacent to a composition, another substrate, or a combination thereof. A personal care article may comprise a contact substrate, non-contact substrate, or combinations thereof. Contact substrates are those on the exterior of the article likely to make direct contact with the target surface, while non-contact substrates are those not likely to make contact with the target surface. A personal care article may be used, for example, on skin, hair, or both. A personal care article may also be used, for example, for cleansing of the skin, cleansing of the hair, shave preparation, post shave treatment, or a combination thereof. A personal care article may be a personal cleansing article. A personal care article may also be reusable.

Adding a substrate to a personal care composition can present its own challenges. A substrate can change the amount of water available to the composition at the outset which can impact lather, rate of consumption, and surfactant release. A substrate can also change the dynamics with the composition during use. For example, the substrate can retain water in close proximity to the composition. It can also impact the composition after use by, for example, limiting the exposure of the composition to the air to inhibit drying after use. All of these factors can be considered when creating a personal care article and the properties of the composition and the article are balanced so that the article has the desired characteristics. This is especially true where the composition and/or article are to be compliant throughout the lifetime of the article.

A personal care article can be compliant. For example, if the article is a personal care article for cleansing the skin, then the article will bend to some degree to more fully contact a curved body part like the arm. Thus, if the personal care article is originally flat with no curve, when applied to the arm for cleansing there would be some amount of bend to better conform to the arm. Oppositely, if the original article is curved such that it would not need to bend to conform to a curved surface like the arm, then it would bend to straighten when applied to a less curved surface like the abdomen. An article may be fully compliant meaning it is capable of completely conforming to the surface to which it is applied.

Compliance of a personal care article can be measured according to the Compliance Test described in more detail below. A personal care article can comprise a compliance value of about 1.50 kg/mm or less. Additional examples of suitable compliance values include from about 0.01 kg/mm to about 1.5 kg/mm; from about 0.03 kg/mm to about 1.0 kg/mm; about 0.10 kg/mm to about 0.75 mm/kg; about 0.10 kg/mm to about 0.6 kg/mm; about 0.05 kg/mm to about 0.5 kg/mm; or about 0.1 kg/mm to about 0.3 kg/mm.

The article and/or composition can become compliant after exposure to water. Thus, a non-compliant article or composition may, after exposure to a liquid, like water, during use, become compliant. If an article or composition becomes compliant by the end of a second simulated use, then it is considered compliant.

Figure 4:
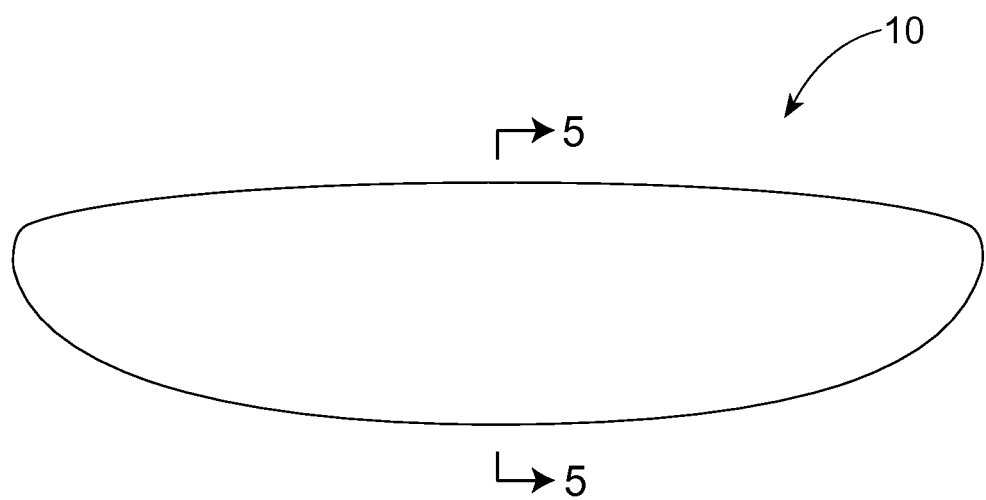
FIG. 4 depicts a side view of a personal care article according to another example.
Figure 5:
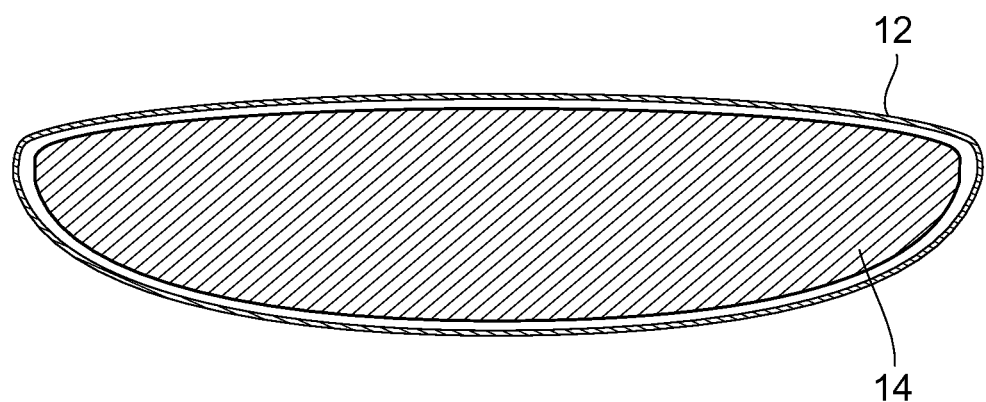
FIG. 5 depicts a cross sectional view of the personal care article of FIG. 4, along line 5-5.

A perspective view of a person care article 10 according to one example is shown in FIG. 1. As shown in FIGS. 4 and 5, a personal care article 10 can comprise a water penetrable first substrate 12 and a personal care composition 14, wherein the water penetrable first substrate 12 is adjacent to the personal care composition 14. The water penetrable first substrate 12 at least partially surrounds the composition 14. In one example, as shown in FIG. 4, a single piece of water penetrable substrate 12 has been wrapped around the personal care composition 14 and sealed (not shown).

Figure 2:
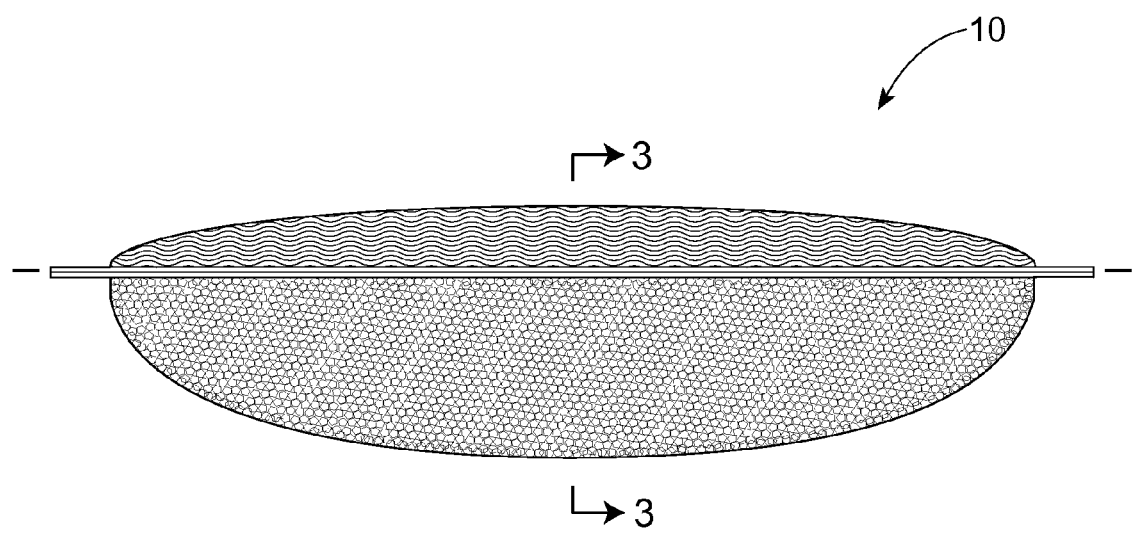
FIG. 2 depicts a side view of a personal care article according to one example.
Figure 3A:
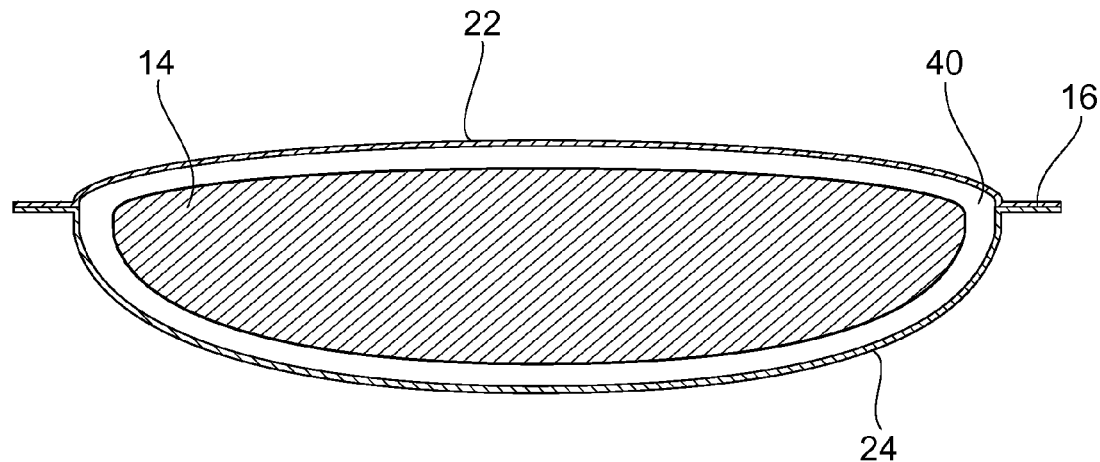
FIG. 3A depicts a cross sectional view of the personal care article of FIG. 2, along line 3-3.

In another example, as illustrated in FIGS. 2 and 3A, a personal care article 10 comprises a personal care composition 14, a first substrate 22 adjacent to the personal care composition 14, and a second substrate 24 adjacent to the personal care composition 14. In one example depicted in FIG. 3A, the seal 16 joining the first and second substrates (22, 24) is only visible on the ends, but actually goes all the way around the personal care composition 14. The first and second substrates (22, 24) may, however, be sealed in other configurations, or, may only be partially sealed so as to form, for example, a pouch. The first and second substrates (22, 24) may be the same or different.

Figure 6:
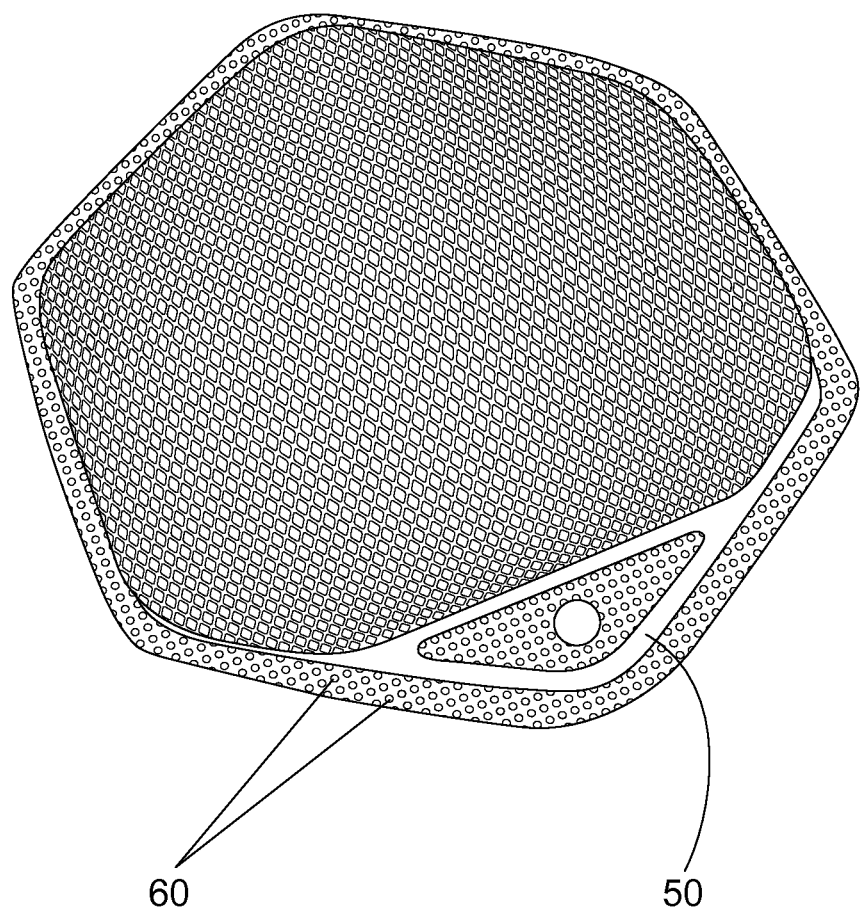
FIG. 6 is a perspective view of an exemplary personal care article.
Figure 7:
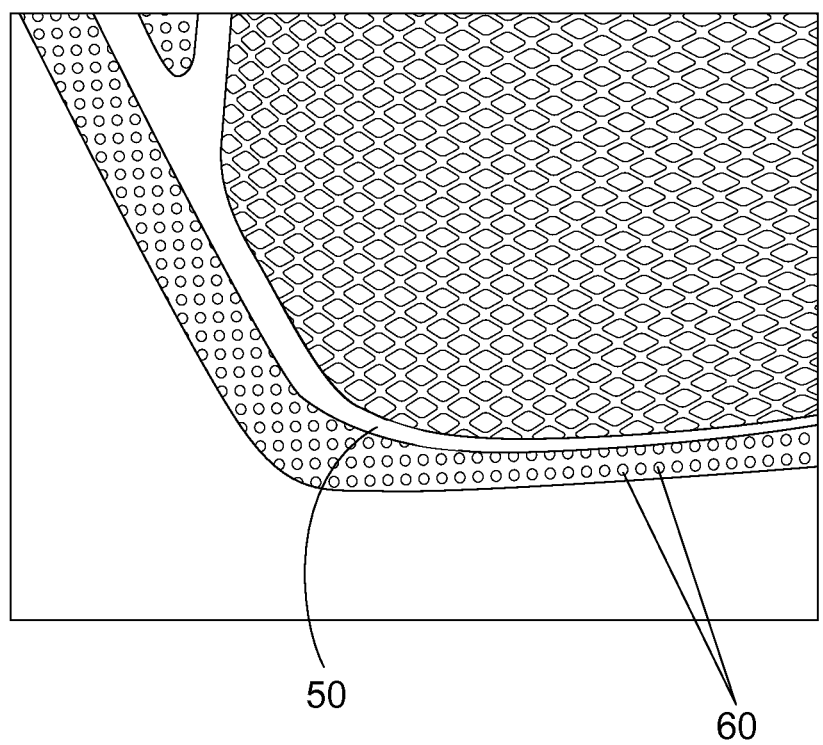
FIG. 7 is a close-up of one corner of the article in FIG. 6.

As can be seen in FIGS. 6 and 7, another exemplary form of sealing involves forming a continuous seal 50 internal to the periphery of the article, where the periphery of the article is sealed in a discontinuous manner 60. The continuous seal 50 internal to the periphery of the article prevents bulk loss of composition from the article and provides sufficient seal strength for maintaining the integrity of the article throughout consumer use. Locating the continuous seal 50 internal to the article periphery is advantageous in that a sealed land area creates a thin hard surface, relative to the inherent substrate properties. This thin hard seal surface when located on the article periphery can cause scratching when used by the consumer. The article periphery can also be left unsealed leaving the distinct substrate layers separate, this result in an unfinished appearance which is not consumer preferred. Having a discontinuous seal 60 on the periphery of the article provides a high quality finished appearance that is consumer preferred while eliminating the formation of a thin hard surface on the periphery of the article. For instance, a 4 mm wide discontinuous seal can be created along the periphery of the article, with the discontinuous pattern being 1 mm by 1 mm squares spaced 2 mm apart. In addition, internal to the article periphery, a 1 mm continuous seal can be created. During manufacturing the article can be trimmed within the discontinuous seal creating a finished article with the desired discontinuous seal width while reducing the risk of inadvertently trimming in the continuous seal area and creating an opening for bulk loss of composition from the article.

In another example only a discontinuous seal 60 may be present along the articles periphery. In this example the pattern and width of the seal are designed to restrict bulk loss of composition from the article.

In an additional example, a seal may be continuous, but interrupted (not shown).

Figure 3B:
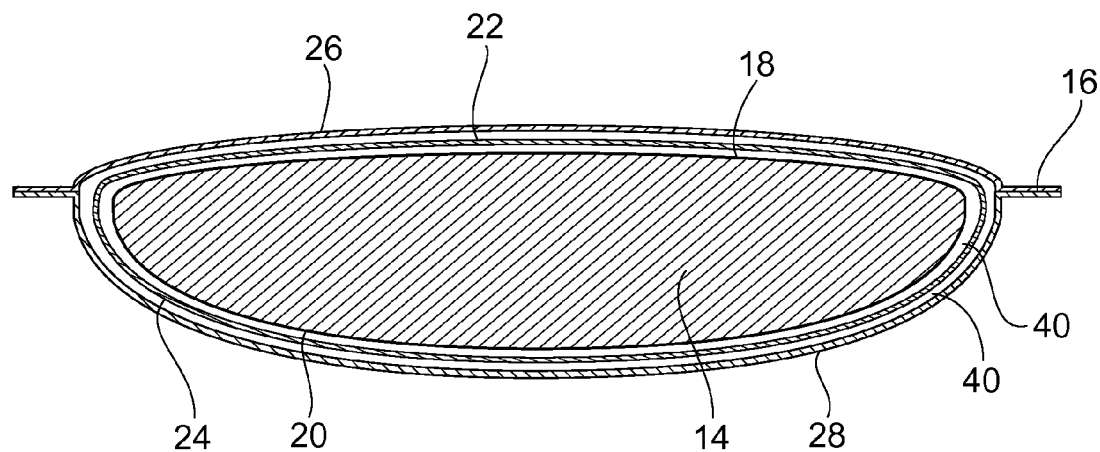
FIG. 3B depicts a cross sectional view of the personal care article of FIG. 2, along line 3-3, where additional substrates have been added.

In another example, as illustrated in FIGS. 2 and 3B, a personal care article 10 comprises a personal care composition 14 having a first side 18 and a second side 20. A first substrate 22 is adjacent to the first side 18, while a second substrate 24 is adjacent to the second side 20. In one example depicted in FIG. 3A, the seal 16 joining the first and second substrates (22, 24) is only visible on the ends, but actually goes all the way around the personal care composition 14. In addition, a first water insoluble substrate 26 is adjacent to the first substrate 22 and a second water insoluble substrate 28 is adjacent to the second substrate 24. The first and second water insoluble substrates (26, 28) may be the same or different. Like the seal of the first and second substrate (22, 24), while only visible on the ends, the seal 16 of the first and second water insoluble substrates (26, 28) goes all the way around the personal care composition 14. The seal 16 of the first and second water insoluble substrate (26, 28) may, however, be sealed in other configurations, or, may only be partially sealed so as to form, for example, a pouch.

The personal care article may also comprise a chamber 40, as seen, for example, in FIGS. 3A and 3B. A chamber is an open area between a substrate and a personal care composition or between a substrate and another substrate, where the substrate is not touching the personal care composition or the other substrate. The substrate(s) may be flexible such that they touch the composition (or another substrate) in some areas and not others. The areas where the substrate is touching or not touching the composition or other substrate may shift as the substrate(s) and composition shift during handling and/or use.

The personal care article can include from about 0.5% to about 25,000%, by weight of total substrate(s), of a personal care composition. In one example, the article comprises greater than 3,500%, by weight of the total substrate(s), of a composition. In other examples, the article comprises greater than 4,000%, by weight of the total substrate(s), of a composition; greater than 4,250%, by weight of the total substrate(s), of a composition; greater than 4,500%, by weight of the total substrate(s), of a composition; greater than 4,750%, by weight of the total substrate(s), of a composition; greater than 5,000%, by weight of the total substrate(s), of a composition; or any combination thereof.

The personal care article may be in any suitable shape, for example, oval, square, rectangular, circular, triangular, hour glass, hexagonal, c-shaped, etc. Furthermore, the article can be sized based upon the desired use and characteristics of the article. An article can range in surface area size, for example, from about a square inch to about hundreds of square inches. An article can also have a surface area of, for example, about 5 in$^2$ to about 200 in$^2$, from about 6 in$^2$ to about 120 in$^2$, or from about 15 in$^2$ to about 100 in$^2$. An article may also have a certain thickness, for example, of from about 0.5 mm to about 50 mm, from about 1 mm to about 25 mm, or preferably from about 2 mm to about 20 mm. There may also be multiple compositions within zones in the article. These are described more fully in U.S. Pat. App. Pub. Nos. 2013/0043145, 2013/0043146, and 2013/0043147.

The article will also have a consumption rate as measured by the Consumption Test. The composition may have a consumption, for example, of about 0.5 g to about 14 g per use; about 0.5 g to about 8 g per use; about 0.5 g to about 7 g per use; or about 0.5 g to about 6 g per use.

A substrate can also comprise a feature. Substrate features can include, for example, design elements such as shapes and letters. Substrate features may reside, for example, within the land portions, the surface aberrations, or a combination thereof and may be located in plane, above plane, or below plane, or combinations thereof relative to either the land portion or surface aberration. Substrates with features out of plane with both the land and surface aberration portions are considered multiplanar substrates. Examples of features can be seen in FIGS. 8 (the "O"'s) and 9 (the stars).

The article 10 may further comprise a hanger 100, see FIG. 1. A hanger 100 will allow the article 10 to be suspended. Suitable hangers can include chords, hooks, loops, twines, strings, elastic bands, etc. and can comprise synthetic /and or natural materials including fibers, and can be molded such as injection molded. A hanger may be a single piece or multiple pieces fastened together. The multiple pieces could have corresponding male and female elements and the fastening mechanisms could include, for example, snaps, buttons, hook and eye, etc.

The article may also further comprise a use indicator 110, see FIG. 1. A use indicator 110 will help signify to a user when the article 10 has reached or is reaching the end of its useful life. A use indicator can take the form of, for example, a strip which changes color as the article is used. Additional examples of use indicators can include printed inks, dyes, pigments, slot or spray coated polymers containing, for example, inks, dyes or pigments.

A. Substrate

A personal care article can comprise at least one substrate. The substrate can enhance cleansing and therapeutic treatment of a surface such as skin and/or hair. For example, by physically coming into contact with the skin and/or hair, the substrate can aid in the cleansing and removal of dirt, makeup, dead skin, and other debris such that the substrate can act as an efficient lathering and/or exfoliating implement but can also be non-abrasive to the skin. A substrate can be a composite (i.e., there are multiple plies to the substrate which may be of the same or different materials). In one example, the substrate can be water insoluble. In other examples, the substrate can be water penetrable. However, the personal care article can comprise both water penetrable substrates and water insoluble substrates.

Substrates can be arranged in many different configurations on an article. Some examples of these configurations can be found, for example, in U.S. Pat. No. 6,491,928; U.S. Pat. App. Pub. Nos. 2013/0043146; 2012/0246851; 2013/0043145; and 2013/0043147.

A substrate can at least partially surround one or more personal care compositions. In other examples, a substrate can entirely surround one or more personal care compositions. A substrate can be in the form of a pouch, pocket, wrap, or any other suitable configuration. A substrate could also at least partially surround or be adjacent to another substrate, and/or entirely surround another substrate.

The substrate can be, for example, a formed film, like a vacuum formed film. The substrate could be a nonwoven (i.e., a natural or synthetic nonwoven including fibrous and nonfibrous nonwovens), which can typically have land regions (i.e., regions that do not allow water and/or personal care composition to pass through) and openings; a woven; a film (e.g., a formed film); a sponge, which can include a natural and/or synthetic sponge (e.g., polymeric mesh sponge), examples of which can include those described in European Patent Application No. EP 702550A1 published Mar. 27, 1996; a polymeric netted mesh (i.e., a "scrim"), examples of which can include those described in U.S. Pat. No. 4,636,419; a batting; spunbond; spunlace; hydroentangled; carded; needlepunch; or any other suitable material. In certain examples, the substrate can be a composite material that can include, for example, one or more plies of the same or different materials such as nonwovens, wovens, films, sponges, scrims, battings, and the like superimposed physically, joined together continuously (e.g., laminated, etc.) in a discontinuous pattern, or by bonding at the external edges (or periphery) of the substrate and/or at discrete loci. Suitable examples for each type of substrate and other suitable substrate materials are described in U.S. Pat. App. Pub. No. 2012/0246851.

Parameters to consider when selecting substrates (e.g., formed films) can include thickness, pattern, polymer stiffness, and permeability. Additional information on such parameters is also described in U.S. Pat. App. Pub. No. 2012/0246851.

A substrate can include one or more openings such that water, the personal care composition, and/or lather, for example, can pass through the substrate. In one example, where a permeable substrate can be adjacent to the personal care composition, water can pass through the water permeable substrate to interact with the personal care composition. As the personal care composition dissolves, it can then also pass through the substrate to be delivered to a target surface (e.g., skin).

In one example, permeability of openings can be selected based on a dissolution half-life of a personal care composition and a desired reusability of the article. For example, when the dissolution half-life of the personal care composition is high, a higher level of permeability can be selected to counteract the high dissolution half-life and provide a desirable consumption rate for the article. Alternatively, when the dissolution half-life of the personal care composition is low, the permeability of the one or more openings or can be lower and still provide a desirable consumption rate for the article. A substrate can include, for example, a permeability of about 1 opening/$cm^2$ or greater, about 10 openings/$cm^2$ or greater, about 100 openings/$cm^2$ or greater, about 500 openings/$cm^2$ or greater, about 1,000 openings/$cm^2$ or greater, about 1,500 openings/$cm^2$ or greater, or any combination thereof.

The openings can be apertures. For example, the one or more openings can include well-defined apertures such as microapertures or macroapertures, holes, perforations, cavities, raised or depressed fibrous and/or nonfibrous regions, gaps between regions, and the like that can enable, for example, water and/or the personal care composition to pass through the substrate.

A substrate can be a contact substrate, which can be a substrate for contacting a target surface (e.g., skin). A substrate can also be a noncontact substrate. Noncontact substrates, for example, can be used to help give a personal care article a desired consumption rate, softness, lather properties, etc.

Figure 8A:
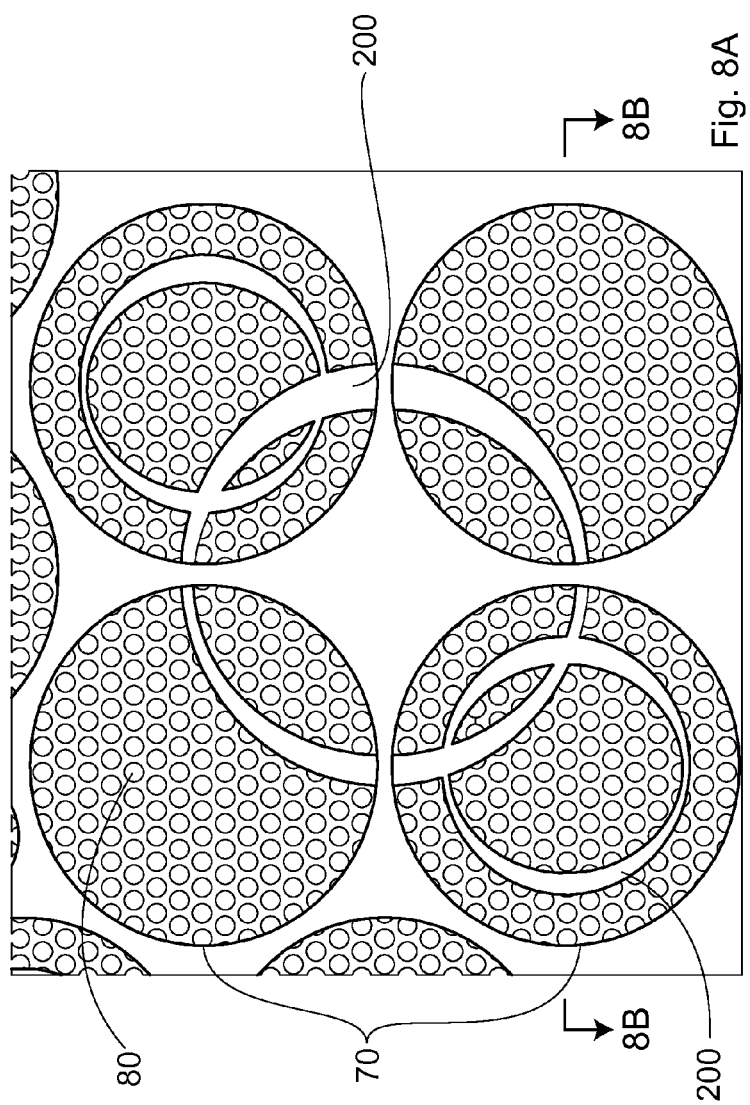
FIG. 8A is a top perspective view of an exemplary substrate.
Figure 8B:
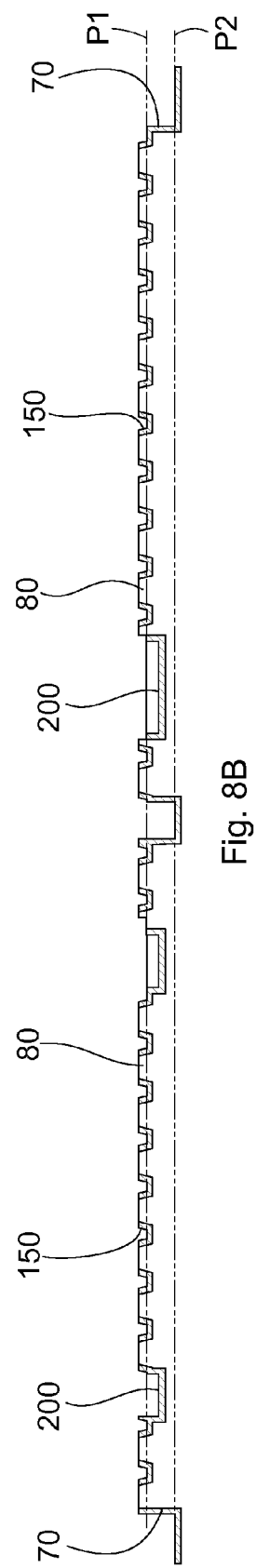
FIG. 8B is a cross sectional view of the exemplary substrate of FIG. 8A, along line 8B-8B.
Figure 10:
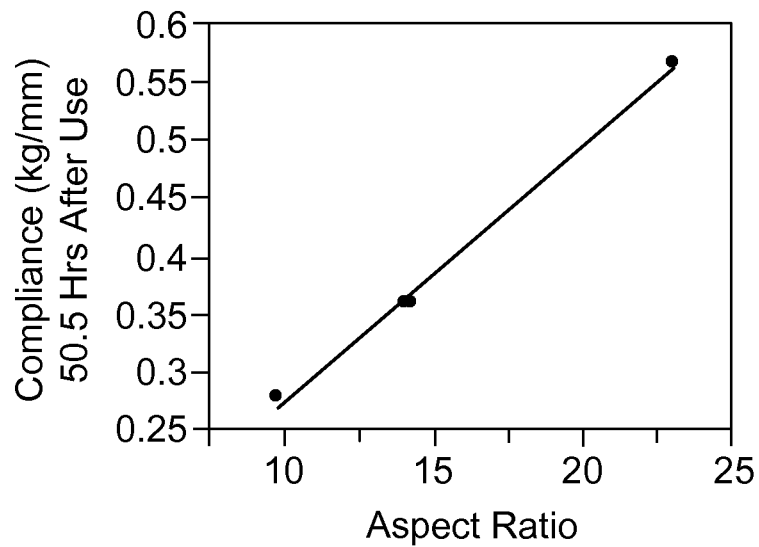
FIG. 10 is a regression of aspect ratio and compliance 50.5 hours after use.
Figure 11:
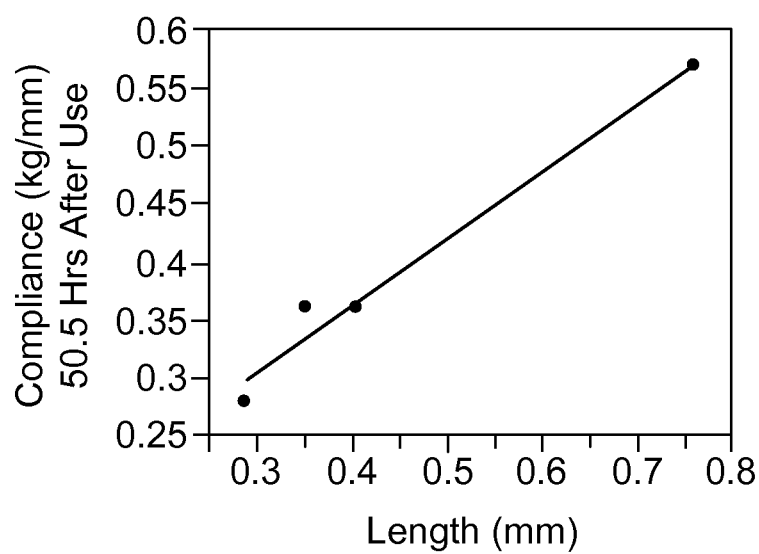
FIG. 11 is a regression of length and compliance 50.5 hours after use.
Figure 12:
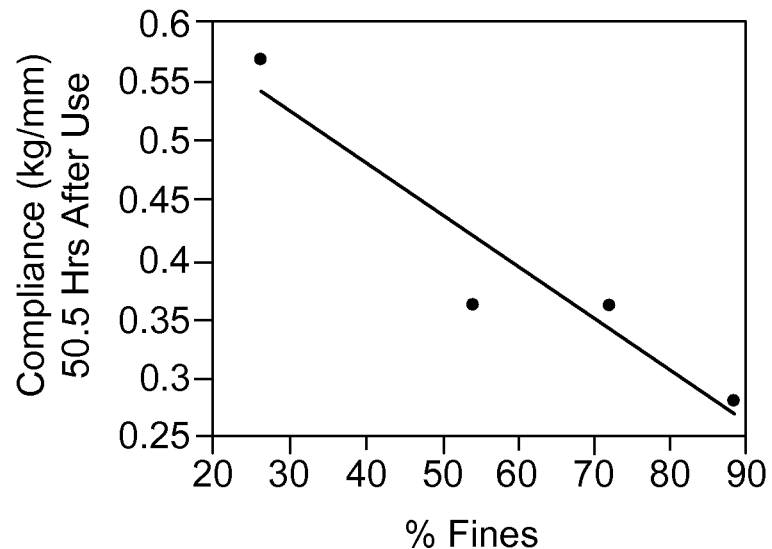
FIG. 12 is a regression of % fines and compliance 50.5 hours after use.
Figure 13:
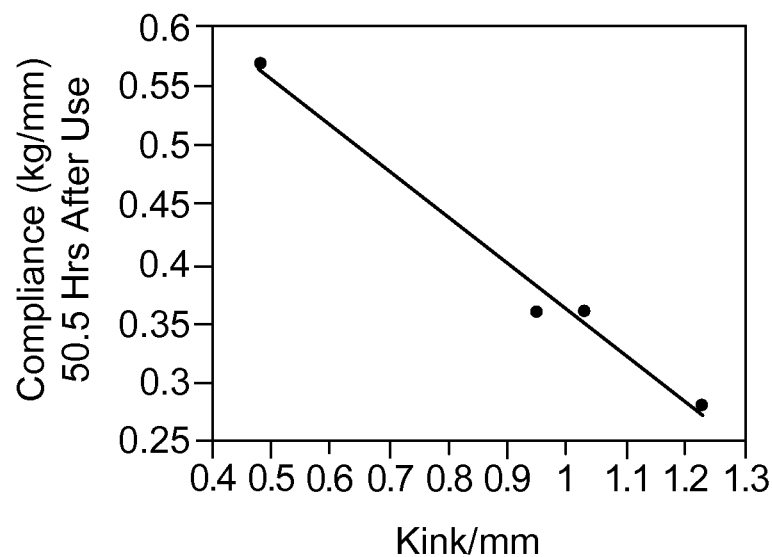
FIG. 13 is a regression of kink and compliance 50.5 hours after use.
Figure 14:
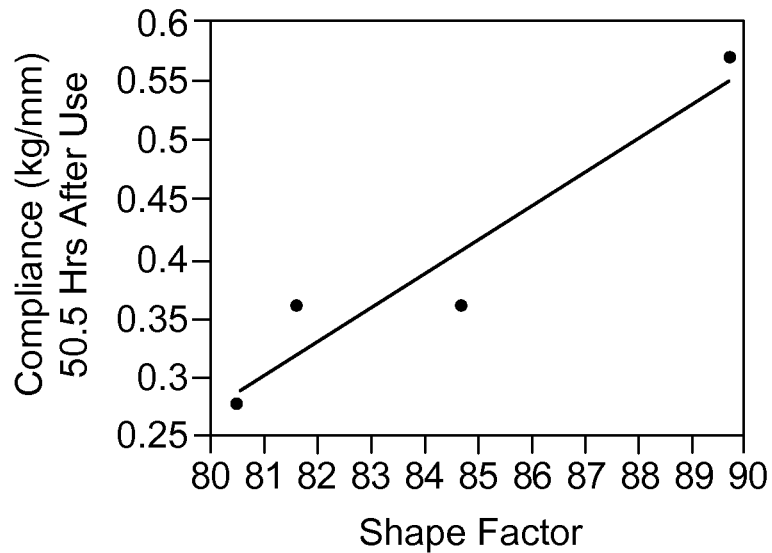
FIG. 14 is a regression of shape factor and compliance 50.5 hours after use.
Figure 15:
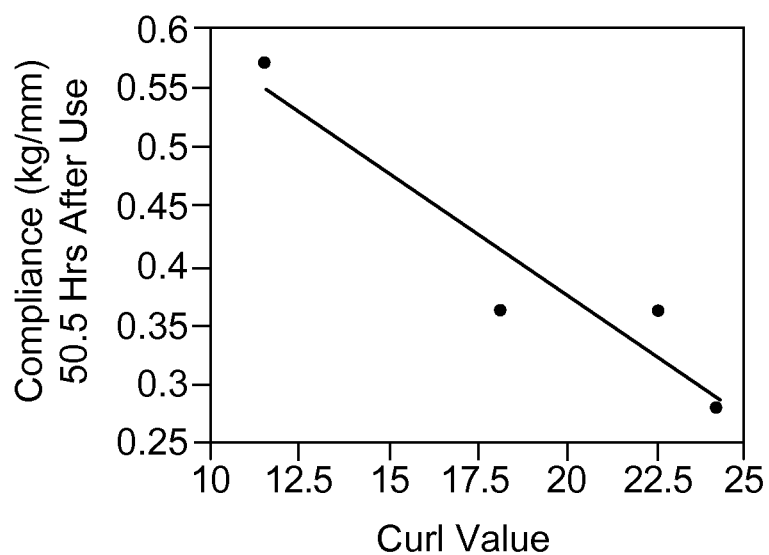
FIG. 15 is a regression of curl value and compliance 50.5 hours after use.

A substrate may also comprise a surface aberration 70, as can be seen in FIGS. 8 and 9. A surface aberration can be a raised portion on a surface of a substrate. It can be readily apparent to the naked eye and can form a geometric pattern on a substrate. In one example, the geometric pattern does not require registration on the assembled article.

Surface aberrations can be from about 700 μm to about 7000 μm in height (the z-direction). Surface aberrations can also be macroapertured.

The surface aberrations provide thickness without itself being a single pore, while the conventional portions of the substrate can provide a larger number of pores to promote lather generation. Particularly, multiplanar substrates with a thickness from about 700 μm to about 7000 μm can allow for enough water, surfactant, and air to pass through such that the sufficient lather can be generated.

Surface aberrations can also provide an exfoliation benefit. In order to provide exfoliation with a monoplaner film you need to create pores with a large diameter, in order to achieve a significant z-dimension. This concentrates the applied force over a smaller contact area with the skin, making the substrate feel scratchy. Conversely, multiplanar films contain surface aberrations with larger z-dimensions. These surface aberrations contribute to the exfoliating properties of the film and more directly control the surface area over which the applied force is distributed, reducing the scratchy perception of the substrate. Additionally, by incorporating a minimum number of pores per square inch, about 10 (local), the issue with a scratchy feel related to pore size can also be abated.

Land area of a substrate can impact consumer acceptance of the product. For example, consumers can view films with larger amounts (e.g. about 55% or more) of land area as looking too much like plastic. In order to combat this consumer perception, a substrate may include more surface aberration area (e.g. about 45% or more).

A substrate may include about 45%, about 50%, about 55%, about 60%, about 65%, about 70%, about 75%, to about 50%, about 55%, about 60%, about 65%, about 70%, about 75%, about 80%, about 85%, about 90%, about 95%, about 98%, or any combination thereof, of surface aberration area. The amount of surface aberration area and land area can be determined by measuring the dimensions geometrically in the X-Y (flat planar) direction for the unit cell of the substrates for their planar projection, for example, with a ruler or a caliper. It may be convenient to use a magnifying technique to measure fine dimensions. Surface aberration and land area can be estimated from geometries of processing equipment used to make the structures, which are usually known from design, although these are only estimates since substrates can shrink or stretch during subsequent processing. Thus, land area and surface aberration area are expressed as a percentage of land (or surface aberration) area within a unit cell divided by the total area of the unit cell. Where the pattern on the substrate is irregular such that no unit cell exists, the percentage of land or surface aberration area is expressed as the amount of land (or surface aberration) area of the article surface utilizing the substrate pattern in question divided by the total area of the article surface utilizing the substrate pattern in question. A surface aberration can be part of a unit cell which is generally the smallest repeating unit (other than pores, if applicable). The calculation is determined with the substrate oriented such that the protuberances or pores are in the upward direction, pointing normal to the viewing plane. For instance a circular aberration motif with a diameter of 0.25 mm and a unit cell area of 0.625 mm² would have a percentage surface area of aberration of approximately 7.85%.

Too much surface aberration area can impact the integrity of a substrate and can, for example, lower the resistance of the substrate to tearing. Thus, the amount of surface aberration area can be balanced among scratchiness, consumer acceptable look, and longevity based on the desired properties of the substrate.

Surface aberrations can be permanent deformations in a substrate, such that after they are formed, no force is required to maintain the raised or depressed state. Surface aberrations can be formed through a process, like, vacuum forming, for example. So, actions like cinching and gathering do not generally form surface aberrations, but puckers in a substrate. These surface aberrations may also contain pores 80. To form a plane, as discussed below, at least some of the surface aberrations will contain at least three protuberances that are not in a row. A surface aberration can have up to about 250,000 protuberances on its surface. A surface aberration can form a pattern or design. For example, the surface aberrations 70 in FIG. 8 are circles and form a repeating pattern, while the surface aberrations 70 in FIG. 9 are hexagons and form a repeating pattern. Surface aberrations can have an area of, for example, about 0.005 cm² or more, about 0.01 cm² or more, or about 0.07 or more.

As can be seen in FIGS. 8 and 9, surface aberrations 70 have edges connecting their surface to the base substrate. These edges are formed during processing of the substrate to make the surface aberrations. During processes like vacuum forming, these edges maintain a similar thickness to that of the substrate before processing. This can help with stability of the substrate when it is processed into rolls. Some processes, like those used to form embossments and debossments, stretch the substrate resulting in edges to the embossments and debossments that are thinner than that of the substrate before processing which can cause issues with stability of the substrate when processing into rolls for transport.

A substrate can also comprise a feature. Substrate features can include, for example, design elements such as shapes and letters. Substrate features may reside, for example, within the land portions, the surface aberrations, or a combination thereof and may be located in plane, above plane, or below plane, or combinations thereof relative to either the land portion or surface aberration. Substrates with features out of plane with both the land and surface aberration portions are considered multiplanar substrates. Examples of features can be seen in FIGS. 8 (the "O"'s) and 9 (the stars).

Surface roughness can be added in the land area, in the portion of surface aberration areas that are closed, and/or on features, of substrates. Creating surface roughness results in a reduction of the gloss of the substrate surface which corresponds to a preferred consumer appearance. Gloss values can be, for example, less than about 3.5 or less than about 2.5.

A substrate can be multiplanar. For example, see FIGS. 8 and 9, where there is a first plane (P1) which is defined by land area on the surface aberrations 70 and a second plane (P2) which is defined by the land area of the base film. A second plane can be, for example, contiguous and repeating and generally non-porous. The second plane can generally be flat or can be flattened merely by placing the substrate on a table. The transition from first plane to second plane (70 in FIG. 8B) can be discrete as in FIGS. 8B and 9B which depict 90 degree angles or the transition can be stepped, tapered or occur at an angle less than about 90 degrees but greater than 0 degrees. A first plane can be, for example, discontinuous like in FIGS. 8 and 9. The first plane can be flat, raised, or even curved, so that it is not planar in the formal geometric sense, and is used to describe a base region from which protrusions can be raised and generally extends in an orthogonal direction to the protrusions and is the same plane as the original film from which the protrusions were raised. Surface aberrations which are similar (in the geometric sense) are considered to be in the same plane even if they are not connected to one another. Where the surface aberrations are dissimilar (for example, different heights from the plane of the original film), then they can create multiple planes.

Features 200, which can be continuous or discrete, can be added to the substrate and can represent additional planes or even add texture, for example patterns like starts, squares, logos can be embossed onto the substrate. Features 200 can also be at the same level of an existing plane, so can be considered part of an existing plane, and not an additional plane. A formed film is considered a planar substrate. A seal on a substrate is usually on such a similar level to an existing plane that it is considered as part of the existing plane and not creating an additional plane.

Some examples of suitable substrates are included below.
1. Formed Films

| Code | Material Description | Caliper and Basis Weight | Pore count/ area; and diameter |
|---|---|---|---|
| F1 | Hydroapertured polyethylene film on 100 mesh screen, white (Tredegar, Inc.) | 166 microns, 24.5 gsm | 1,780/cm² — |
| F2 | Vacuum formed polyethylene film, white (SSRIS-CPM, Tredegar, Inc.) | 560 microns, 24.5 gsm | 115/cm² — |
| F3 | Vacuum formed polyethylene film, white 22 Hex (Tredegar, Inc.) | 560 microns, 24.4 gsm | 91/cm² ~500 micron |
| F4 | Vacuum formed polyethylene film, blue 11.2 Hex (Tredegar, Inc.) | 935 microns, 29.4 gsm | 22.2/cm² 1.1 mm |
| F5 | Vacuum formed polyethylene film, green (Tredegar, Inc.) | 670 microns, 36.0 gsm | 49/cm² 0.9 mm |
| F6 | Vacuum formed polyethylene film, white (Tredegar, Inc.) | 33.5 gsm | 12.6/cm² 1 mm |
| F7 | Vacuum formed polyethylene film 40 Hex | 418 microns, 35.8 gsm | 285/cm² — |
| F8 | Vacuum formed polyethylene film 8.75 Hex | 950 microns, 37.4 gsm | |

Caliper: ASTM D645
Air Permeability: ASTM D737

2. Fibrous Nonwovens

| Code | Material Description | Basis Weight |
|------|---------------------|--------------|
| N1 | Spunlaid hydroentangled 100% PP (Avgol Nonwovens, NC, USA) | 47 gsm |
| N2 | Carded, calendar bonded all bicomponent PP/PE fiber (Fiberweb Inc., TN, USA) | 32 gsm |
| N3 | Spunbond, overbonded 100% PP (Experimental nonwoven) | 37 gsm |
| N4 | Carded, through air bonded 30/30/40 PP/Bicomponent PP-PE/Rayon (calendar patterned) | 62 gsm |

3. Fibrous Nonwoven Battings

| Code | Material Description | Caliper; and Basis Weight |
|------|---------------------|---------------------------|
| B1 | Quilter's Fusible batting, low loft all polyester (Fairfield Processing, Danbury, CT, USA) | 2.50 mm, 160 gsm |
| B2 | Quilter's Fusible batting, low loft all polyester, ½ thickness (peeled) | 1.21 mm, 80 gsm |
| B3 | PROEF 12-334 polyester-bicomponent fiber blend batting (Libeltex, Belgium) | 1.54 mm, 100 gsm |
| B4 | PROEF 12-370 dual layer PET/copet bico and PP fibers; bulk layer with standard PET/coPET bico trilobal fibers (Libeltex, Belgium) | 0.60 mm, 55 gsm |
| B5 | Dry Web T30 SC batting, hollow PET + bico PET/PE fiber blend, through air bonded (Libeltex, Belgium) | 0.41 mm, 35 gsm |
| B6 | PROEF 12-372 batting, coarse polyester and PE/PET bico fibers (Libeltex, Belgium) | 0.55 mm, 50 gsm |
| B7 | Dry Web T23W batting, coarse polyester and bico fiber mix (Libeltex, Belgium) | 0.56 mm, 50 gsm |

4. Laminate Films

| Code | Material Description | Basis Weight |
|------|---------------------|--------------|
| L1 | Formed film nonwoven laminate | 34 gsm |

5. Multiplanar Films

| Example | pattern | design or post processing | Thickness (micron) | Number of Pores per Sq. In. |
|---------|---------|---------------------------|--------------------|-----------------------------|
| Multiplanar 1 | 30 hex | Multiplanar with star shape feature and hexagonal land area, land area 7% | 1724 | 1035 (local) |
| Multiplanar 2 | 30 hex | Multiplanar with circular raised areas further with letter 'O' feature | 2640 | 1035 (local) |
| Multiplanar 3 | 30 hex | Biplanar with hexagonal pattern | 2514 | 1035 (local) |
| Multiplanar 4 | 30 hex | Biplanar | 1597 | 1035 (local) |
| Multiplanar 5 | | Biplanar with circular raised areas and 30% HDPE resin, 0.025 in. plane height, gloss of 3.2 | 1985 | 1840 (local) |
| Multiplanar 6 | | Biplanar with circular raised areas and 30% HDPE resin, 0.040 in. plane height, gloss of 2.9 | 2080 | 1840 (local) |
| Multiplanar 7 | | Biplanar with circular raised areas, 30% HDPE resin, 0.055 in. plane height, gloss of 2.5 | 3550 | 1840 (local) |
| Multiplanar 8 | | Biplanar with circular raised areas, 30% land area | 2012 | 1840 (local) |
| Multiplanar 9 | | Biplanar with circular raised areas, 44% land area | 2421 | 1840 (local) |

EXAMPLES

The following examples further describe and demonstrate compositions and articles within the scope of the present invention. In the following examples, all ingredients are listed at an active level. The examples are given solely for the purpose of illustration and are not to be construed as limitations of the personal care article or components thereof such as the composition or substrate, as many variations thereof are possible without departing from the spirit and scope disclosed herein.

Examples D1-D14 are made in the following manner. Cocamidopropyl betaine was combined with preservatives in a tank equipped with an impeller mixing blade. Sodium cocylisethionate, cocoamide monoethanolamine, cellulose fibers, zinc pyrithione (when included), and fragrance were combined in an amalgamator typically employed in bar soap making. The cocamidopropyl betaine/preservative solution was added into the amalgamator and the composition was mixed until visually homogeneous. The resulting amalgamated composition was then transferred to a conventional bar soap 3 roll mill and passed through the mill 2 times. The resulting milled composition was then passed through a conventional bar soap plodder and cut to the desired length.

Comparative example C1 can be prepared by combining each of the ingredients listed in the table below and speed mixing the mixture at 2,000 rpm for 30 seconds to generate a homogeneous composition.

Approximately, 50 g of each composition was sealed within substrates forming a three dimensional article with dimensions of approximately 7.5 cm×10 cm×1.3 cm, with the interior substrate being example substrate F7, one of the contact substrates being example substrate L1 and the other contact substrate being Multiplanar 2.

| Inventive Example Number | Hygroscopic Material | Sodium cocoyl isethionate | Cocamidopropyl betaine | cocoamide monoethanolamine | Preservatives | Zinc Prythione | Fragrance | Hygroscopic material | Water |
|---|---|---|---|---|---|---|---|---|---|
| Example D1 | Example HG4 | 18.00% | 9.45% | 11.1% | 0.34% | 0.34% | 3.43% | 17.14% | 36.63% |
| Example D2 | Example HG4 | 43.50% | 5.51% | 23.0% | 0.20% | 0.20% | 2.00% | 10.00% | 7.71% |
| Example D3 | Example HG4 | 36.00% | 7.35% | 19.7% | 0.27% | 0.27% | 2.67% | 13.33% | 13.83% |
| Example D4 | Example HG4 | 21.00% | 11.03% | 13.0% | 0.40% | 0.40% | 4.00% | 20.00% | 26.07% |

-continued

| Inventive Example Number | Hygroscopic Material | Sodium cocoyl isethionate | Cocamidopropyl betaine | cocoamide monoethanolamine | Preservatives | Zinc Prythione | Fragrance | Hygroscopic material | Water |
|---|---|---|---|---|---|---|---|---|---|
| Example D5 | Example HG4 | 18.38% | 9.65% | 11.4% | 0.35% | 0.35% | 3.50% | 30.00% | 22.81% |
| Example D6 | Example HG6 | 20.1% | 8.8% | 12.3% | 0.36% | — | 4% | 30% | 20.50% |
| Example D7 | Example HG6 | 20.1% | 11.7% | 12.3% | 0.48% | — | 4% | 20% | 27.33% |
| Example D8 | Example HG3 | 20.1% | 11.7% | 12.3% | 0.48% | — | 4% | 20% | 27.33% |
| Example D9 | Example HG4 | 20.1% | 11.7% | 12.3% | 0.48% | — | 4% | 20% | 27.33% |
| Example D10 | Example HG5 | 20.1% | 11.7% | 12.3% | 0.48% | — | 4% | 20% | 27.33% |
| Example D11 | Example HG2 | 24.4% | 14.2% | 14.9% | 0.58% | — | 4% | 3.03% | 33.98% |
| Example D12 | Example HG2 | 23.7% | 13.8% | 14.5% | 0.56% | — | 4% | 5.88% | 32.86% |
| Example D13 | Example HG3 | 24.0% | 13.9% | 14.7% | 0.57% | — | 4% | 4.76% | 33.30% |
| Example D14 | Example HG3 | 23.7% | 13.8% | 14.5% | 0.56% | — | 4% | 5.88% | 32.86% |

| Comparative Example Number | Hygroscopic Material | Sodium Laureth Sulfate | Cocoamidopropyl betaine | Glycerin | Preservatives | Laponite Clay | Fragrance | Water |
|---|---|---|---|---|---|---|---|---|
| Example C1 | Laponite Clay | 18.0% | 2.4% | 21.7% | 0.6% | 43.5% | 0.9% | 12.9% |

The article compliance and composition rheology values of the above example compositions are:

| | Article Compliance (kg/mm) | | | Composition Rheology | | | |
|---|---|---|---|---|---|---|---|
| Composition | | | | | Zero shear | | Power Law |
| Example Number | Prior To Use | 30 min After Use | 50.5 Hrs After 1 simulated Use | Viscosity (PaS) | viscosity (PaS) at 1 (1/s) | Rate Index | yield stress |
| Example D1 | 0.20 | 0.17 | 0.33 | — | — | — | — |
| Example D2 | 1.16 | 0.61 | 1.04 | — | — | — | — |
| Example D3 | 0.52 | 0.32 | 0.61 | — | — | — | — |
| Example D4 | 0.22 | 0.18 | 0.34 | — | — | — | — |
| Example D5 | 0.49 | 0.45 | 0.57 | — | — | — | — |
| Example D6 | 0.45 | 0.51 | 0.77 | 2.35E+06 | 468.2 | 0.044 | 2228 |
| Example D7 | 0.18 | 0.12 | 0.28 | 1.94E+06 | 850.7 | 0.071 | 1073 |
| Example D8 | 0.33 | 0.34 | 0.57 | 1.46E+06 | 525.8 | 0.057 | 3197 |
| Example D9 | 0.23 | 0.23 | 0.36 | 1.39E+06 | 534.8 | 0.061 | 1843 |
| Example D10 | 0.13 | 0.19 | 0.36 | 1.62E+06 | 580.6 | 0.066 | 854 |
| Example D11 | 0.10 | 0.11 | 0.23 | 5.41E+05 | 333.3 | 0.080 | 263 |
| Example D12 | — | — | — | — | — | — | — |
| Example D13 | 0.12 | 0.14 | 0.23 | 7.37E+05 | 471.2 | 0.076 | 402 |
| Example D14 | — | — | — | — | — | — | — |
| Example C1 | 0.12 | 0.11 | 1.63 | 1.84E+06 | 644.2 | 0.051 | 3364 |

Test Methods a) Compliance Test

To measure the compliance of an article or composition prior to use, use a Texture Analyzer TA-XT2i (Texture Technologies Corp, NY, USA) equipped with at least a 5 kg load cell and a 0.75 inch ball probe at ambient conditions. Start the test with the probe above but not in contact with the article or composition and use a 2 gram trigger force to commence data collection for both force and distance (i.e., the zero depth point begins at 2 gram-force). Measure a compressive force (kg) at a compression rate of 1 mm/sec over a depth of 5 mm, ensuring that the personal care article or composition form a flat surface over contact area with the ball probe, near the center of the article or composition. Repeat measurements as needed (e.g., at least 3 times) to obtain a representative average value. To determine the compliance of the article or composition divide the maximum observed force (kg) by the maximum compression depth (5 mm). When using a 5 kg load cell some samples may exceed capacity, in this case the maximum compression depth will be less than the set depth of 5 mm, specified in the procedure. Compliance of the article includes a measured force contribution of both the composition and substrate components. If thick or lofty substrates are used such that the probe does not substantially engage a composition component, or if the composition is distributed heterogeneously, the test is performed in a region and to a depth such that the composition component is a substantial contributor to the measured compliance. For example, if thick or lofty substrates are used in an article, the trigger force can be increased until the zero point is within at least about 0.5 mm of the composition.

To measure compliance after a simulated bath/shower use a rotary tumbler (Lortone, Inc., Seattle, Wash., USA model 33B or equivalent) with 4 in. diameter by 4 in. deep cylindrical rubber housing having 825 cc internal volume. The housing revolves on the tumbler at 43 rpm. Obtain a supply of water at about 7.5 grains water hardness and conductivity between 100 to not more than 400 microSemens per centimeter (μS/cm) and heat in a reservoir beaker to 45° C. Maintain the water reservoir at the target temperature within 1 degree. Add 200.0 gm of water from the reservoir to the housing. Weigh an article or composition to obtain the initial weight, and add the article or composition to the housing. Seal the housing with its accompanying watertight lid and place the sealed housing onto the rotary tumbler for 3 minutes. Remove the housing, remove the housing lid, and retrieve the article or composition.

Hang the article or composition to dry under controlled temperature (20-25° C.) and relative humidity (50-60%) with no direct air circulation applied to articles. Take compliance measurements as a function of time. The first time point after simulated use should be no sooner than 5 min after the product has been removed from the rotary tumbler and hung to dry. The final time point can be taken at any point as desired or instructed. For example, the final point can be taken after 15 minutes of drying after one use; after 20 minutes of drying after one use; after 30 minutes of drying after one use; after 60 minutes of drying after one use; after 3 hours of drying after one use; after 5 hours of drying after one use; after 12 hours of drying after one use; after 25 hours of drying after one use; or after 48 hours of drying after one use. When measuring compliance after multiple simulated uses, dry the composition or article for 5 minutes between each simulated use and after the final simulated use, unless the drying time is otherwise specified. For example, to measure compliance after 2 simulated uses, the composition would be put through a simulated use cycle, dried for 5 minutes, put through the second simulated use cycle, dried for 5 minutes and then the compliance measured.

b) Dissolution Rate Test

Obtain a straight walled glass beaker having an inside diameter (i.d.) of 63 mm and an inside height of 87 mm, (e.g., Pyrex 250 mL (No. 1000) which are widely available). Pour 150 grams of distilled water at ambient temperature (75° F.) into the beaker and add a Teflon® coated magnetic stir bar to the beaker. (Note: The stir bar can be nominally 1.5 inches long×5/16 inches diameter, octagonally-shaped as viewed from the end, and can have a 1/16 in. wide molded pivot ring around its center where the diameter can be about 0.35 in.) Examples of a suitable stir bar can include Spinbar® magnetic stir bars available from Sigma Aldrich Corp. worldwide including Milwaukee, Wis., USA and at www.sigmaaldrich.com.

Measure and record the water conductivity of the water using a conductivity meter (e.g., a Mettler-Toledo SevenMulti meter with InLab740 probe). (Note: The conductivity of the water should be about 2 microSemens/cm (uS/cm) or less to indicate a low level of dissolved solids present.) Remove the conductivity probe from the water and place the beaker onto a digitally controlled laboratory stirrer, for example Ika® Werke RET Control-visc available (e.g., from DivTech Equipment Co, Cincinnati, Ohio, USA). Center the beaker on the stirrer and turn the stirrer on to obtain a constant rotation speed of 500 rpm to establish a vortex in the water which measures about 3 cm depth from highest point of water at the beaker edge to lowest point of air at the vortex center. Observe the vortex from above to ensure the beaker is centered and that the magnetic stir bar is centered in the vortex. Weigh 1.0 grams of a composition pressed or formed together as a single unit and add it to the water near the beaker edge but not touching the beaker edge. Begin a timer and allow the water with composition to stir for 1 minute.

Turn off the stirrer. Insert the conductivity probe into the water in a location away from any undissolved material. Allow a measurement to stabilize for a few seconds and record conductivity. Turn the stirrer back on. Restart the timer as the digital readout passes 250 rpm. After an additional 1 minute has elapsed, turn off the stirrer and measure and record conductivity in the same manner as above. Turn the stirrer back on. Restart the timer as the digital readout passes 250 rpm. Repeat the process until a conductivity reading has been obtained every minute of stirring, for 5 minutes.

After taking a 5 minute conductivity reading, cap the beaker with a suitable watertight cover (e.g., plastic wrap). Shake the beaker vigorously for about 1 minute to dissolve remaining solids, using a vortex type agitator and/or mild heating in addition if necessary until all soluble components are observed dissolved by visible inspection. Cool the solution to less than 80° F. prior to the final measurement. Uncap the beaker, measure conductivity and record the value as a final conductivity.

Calculate the fractional dissolution (f) at each time point by the equation: f=(conductivity−water conductivity)/(final conductivity−water conductivity)

Calculate the dissolution half-life by fitting the fractional dissolution time series (6 points from 0 to 5 minutes) to a second order polynomial and calculate an interpolated or extrapolated result for a time at which a composition is half dissolved (i.e., f=0.5).

Dissolution half-life can be a measure of the propensity of a composition to resist solubilization by water. Bars of soap, for example, can have a dissolution half-life of 21.1 minutes (Ivory®™ Soap), exhibiting longevity and low consumption rate during use without a need for substrates as barriers to permeability. Liquid body wash can have a dissolution half-life of less than ½ minute and can be unsuitable as a composition for such articles.

c) Consumption Test

To measure the Consumption Rate of a personal care article or composition per simulated use as noted in this test method (not the Compliance test method), use a rotary tumbler (Lortone, Inc., Seattle, Wash., USA model 33B or equivalent) with a 4 in. diameter by 4 in. deep cylindrical rubber housing having 825 cc internal volume. The housing revolves on the tumbler at 43 rpm. Obtain a supply of tap water at about 7.5 grains water hardness and conductivity between 100 to not more than 400 microSemens per centimeter (μS/cm) and heat in a reservoir beaker to 45° C. Maintain the water supply at the target temperature within 1 degree for the test duration. Add 200.0 g water from the reservoir to the housing. Weigh an article or composition to obtain the initial weight, and add the article or composition to the housing. Seal the housing with its accompanying watertight lid and place the sealed housing onto the rotary tumbler for exactly 3 minutes. Remove the housing, remove the housing lid, and retrieve the article or composition. Stir the remaining water in the housing for a few seconds and measure its conductivity and temperature using a Mettler Toledo Seven multimeter with InLab 740 probe or equivalent. Dry the article or composition surface by pressing, not rubbing, using paper towels with light hand pressure for about 30 seconds, until it is dry to the touch and transfers no more visible water to a dry paper towel using the same pressure at any point on its surface or edges. If the article or composition transfers partially dissolved or dissolving components in addition to liquid water (e.g., if a composition is a conventional bar soap it may transfer paste-like material), the transferred components are to be removed and the article or composition is considered dry when visible transfer is no longer evident. Weigh the article or composition. Repeat this with the same article or composition five times. Subtract the weight after the fifth cycle from the weight after the second cycle and divide by 3 to obtain the consumption rate reported in units g/use.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compliant personal care article, comprising:
   a) a composition comprising:
      i) from about 20% to about 80%, by weight of the composition, of a surfactant; and
      ii) from about 3% to about 40%, by weight of the composition, of a water insoluble hygroscopic filament comprising a fiber and a fine; and
      iii) a solvent; and
   b) a water insoluble substrate;
      wherein the composition is at least partially surrounded by the substrate and the article has a compliance value of about 0.01 kg/mm to about 1.5 kg/mm before a simulated use; and
      wherein the substrate in a multiplanar film.

2. The compliant personal care article of claim 1, wherein the article has a compliance value before a simulated use of about 0.10 kg/mm to about 0.75 kg/mm.

3. The compliant personal care article of claim 1, wherein the article has a compliance value of about 0.01 kg/mm to about 1.5 kg/mm after 15 minutes of drying after one simulated use.

4. The compliant personal care article of claim 1, wherein the article has a compliance value after drying for 12 hours after 10 simulated uses of about 0.10 kg/mm to about 0.75 kg/mm.

5. The compliant personal care article of claim 1, wherein the composition is in the form of a soft solid.

6. The compliant personal care article of claim 1, wherein the composition comprises from about 5% to about 50%, by weight of the composition, of the solvent.

7. A compliant personal cleansing article, comprising:
   a) from about 40% to about 99.6%, by weight of the article, of a cleansing composition, comprising;
      i) from about 20% to about 80%, by weight of the composition, of a surfactant;
      ii) from about 3% to about 40%, by weight of the composition, of a fine, fiber, or filament, comprising cellulose; and
      iii) a solvent; and
   b) a multiplanar film at least partially surrounding the composition;
      wherein the article has a compliance value of about 0.01 kg/mm to about 1.5 kg/mm before a simulated use.

8. The compliant personal cleansing article of claim 7, wherein the surfactant comprises cocoamide monoethanolamine, cocoamidopropyl betaine, decyl glucoside, lauryl glucoside, an alkyl sulfate, or a combination thereof.

9. The compliant personal cleansing article of claim 8, wherein the composition comprises the filament and the filament comprises from about 1% to about 95%, by weight of the filament, of fines, and from about 5% to about 99%, by weight of the filament, of fibers.

10. The compliant personal cleansing article of claim 9, wherein the article has a compliance value of 0.01 kg/mm to about 1.5 kg/mm after 12 hours of drying after 15 simulated uses.

11. The compliant personal cleansing article of claim 10, wherein the composition is in the form of a soft solid.

12. The compliant personal cleansing article of claim 11, wherein the composition comprises from about 5% to about 50%, by weight of the composition, of the solvent.

13. The compliant personal cleansing article of claim 12, wherein the film comprises a surface aberration.

14. The compliant personal cleansing article of claim 13, wherein the surface aberration comprises a pore.

\* \* \* \* \*